(12) United States Patent
Kopelman

(10) Patent No.: US 11,076,856 B2
(45) Date of Patent: Aug. 3, 2021

(54) ANASTOMOSIS DEVICE

(71) Applicant: Mor Research Applications Ltd., Tel-Aviv (IL)

(72) Inventor: Doron Kopelman, Caesarea (IL)

(73) Assignee: Mor Research Applications Ltd., Tel-Aviv (IL)

( * ) Notice: Subject to any disclaimer, the term of this patent is extended or adjusted under 35 U.S.C. 154(b) by 97 days.

(21) Appl. No.: 16/303,188

(22) PCT Filed: May 23, 2017

(86) PCT No.: PCT/IL2017/050572
§ 371 (c)(1),
(2) Date: Nov. 20, 2018

(87) PCT Pub. No.: WO2017/203523
PCT Pub. Date: Nov. 30, 2017

(65) Prior Publication Data
US 2019/0216460 A1    Jul. 18, 2019

Related U.S. Application Data

(60) Provisional application No. 62/340,049, filed on May 23, 2016, provisional application No. 62/427,179, filed on Nov. 29, 2016.

(51) Int. Cl.
*A61B 17/11* (2006.01)
*A61B 17/12* (2006.01)
(Continued)

(52) U.S. Cl.
CPC ........... *A61B 17/1114* (2013.01); *A61B 17/11* (2013.01); *A61B 17/1227* (2013.01);
(Continued)

(58) Field of Classification Search
CPC . A61B 17/1114; A61B 17/11; A61B 17/1227; A61B 17/12136; A61B 17/32;
(Continued)

(56) References Cited

U.S. PATENT DOCUMENTS 5,476,506 A    12/1995 Lunn
5,634,936 A    6/1997 Linden et al.
(Continued)

FOREIGN PATENT DOCUMENTS

EP        2578184        4/2013
WO    WO 2008/040582    4/2008
(Continued)

OTHER PUBLICATIONS

International Preliminary Report on Patentability dated Dec. 6, 2018 From the International Bureau of WIPO Re. Application No. PCT/IL2017/050572. (11 Pages).
(Continued)

*Primary Examiner* — Anh T Dang

(57) ABSTRACT

According to some embodiments there is provided an anastomosis device configured to reduce leakage, comprising: a first set of rings sized to be positioned at a first tissue wall; a second set of rings sized to be positioned at a second tissue wall adjacent the first tissue wall; and an element configured to draw the ring sets towards each other; wherein each set of rings comprises an inner ring, an outer ring, and a coupling for aligning the inner and outer rings with respect to each other; wherein the inner ring applies a first pressure onto the tissue wall which is sufficient to gradually form a passage between the first and second tissue walls; and the outer ring applies a second pressure onto the tissue wall, the second pressure applied radially outwardly relative to the first pressure, the second pressure sufficient to reduce leakage in a vicinity of the passage.

25 Claims, 22 Drawing Sheets

(51) Int. Cl.
*A61B 17/32* (2006.01)
*A61B 17/122* (2006.01)
*A61B 90/00* (2016.01)
*A61B 17/08* (2006.01)
*A61B 17/3205* (2006.01)
*A61B 17/115* (2006.01)
*A61B 17/00* (2006.01)

(52) U.S. Cl.
CPC ........ *A61B 17/12136* (2013.01); *A61B 17/32* (2013.01); *A61B 17/083* (2013.01); *A61B 17/115* (2013.01); *A61B 17/32053* (2013.01); *A61B 2017/00022* (2013.01); *A61B 2017/00084* (2013.01); *A61B 2017/00106* (2013.01); *A61B 2017/00557* (2013.01); *A61B 2017/00818* (2013.01); *A61B 2017/00867* (2013.01); *A61B 2017/00876* (2013.01); *A61B 2017/081* (2013.01); *A61B 2017/1139* (2013.01); *A61B 2017/12004* (2013.01); *A61B 2090/065* (2016.02)

(58) Field of Classification Search
CPC ............ A61B 17/115; A61B 2090/065; A61B 2017/1139; A61B 2017/00557; A61B 2017/00818; A61B 2017/00876

See application file for complete search history.

(56) References Cited

U.S. PATENT DOCUMENTS

| | | |
|---|---|---|
| 6,099,506 A | 8/2000 | Macoviak et al. |
| 7,771,446 B2 | 8/2010 | Rutter |
| 2004/0044364 A1 | 3/2004 | DeVries et al. |
| 2004/0092796 A1 | 5/2004 | Butler et al. |
| 2006/0167482 A1 | 7/2006 | Swain et al. |
| 2007/0173928 A1 | 7/2007 | Morsi |
| 2007/0276378 A1 | 11/2007 | Harrison et al. |
| 2008/0114384 A1 | 5/2008 | Chang et al. |
| 2008/0243151 A1 | 10/2008 | Binmoeller et al. |
| 2009/0093752 A1 | 4/2009 | Richard et al. |
| 2009/0234248 A1 | 9/2009 | Zand et al. |
| 2010/0036399 A1 | 2/2010 | Viola |
| 2011/0124970 A1 | 5/2011 | Kleyman |
| 2012/0065652 A1 | 3/2012 | Cully et al. |
| 2012/0136426 A1 | 5/2012 | Phan et al. |
| 2012/0273548 A1 | 11/2012 | Ma et al. |
| 2013/0253550 A1 | 9/2013 | Beisel et al. |

FOREIGN PATENT DOCUMENTS

| | | |
|---|---|---|
| WO | WO 2012/007042 | 1/2012 |
| WO | WO 2012/007044 | 1/2012 |
| WO | WO 2013/050049 | 4/2013 |
| WO | WO 2014/055193 | 4/2014 |
| WO | WO 2017/203523 | 11/2017 |

OTHER PUBLICATIONS

International Search Report and the Written Opinion dated Aug. 20, 2017 From the International Searching Authority Re. Application No. PCT/IL2017/050572. (20 Pages).

US 11,076,856 B2

ANASTOMOSIS DEVICE

RELATED APPLICATIONS

This application is a National Phase of PCT Patent Application No. PCT/IL2017/050572 having International filing date of May 23, 2017, which claims the benefit of priority under 35 USC § 119(e) of U.S. Provisional Patent Application Nos. 62/340,049 filed on May 23, 2016 and 62/427,179 filed on Nov. 29, 2016. The contents of the above applications are all incorporated by reference as if fully set forth in their entirety.

TECHNICAL FIELD

Aspects of disclosed embodiments relate to anastomosis, and, more particularly, but not exclusively, to reduced-leakage anastomosis.

BACKGROUND

Publication number WO 2012007042 discloses "An anastomosis device (11) for a cholecystoenterostomy comprises a first ring portion (14) intended to be placed inside a gallbladder (8), a second ring portion (15) intended to be placed inside a target portion (12) of an intestine, wherein the [1] anastomosis device (11) is shaped to determine a passage hole (16) in the gallbladder wall and intestinal wall at the cholecystoenterostomy (13) and at least the first ring portion (14) is time-dependently shape changeable such that the bulk of individual pieces of the first ring portion (14) becomes smaller than the passage hole (16)" (Abstract).

SUMMARY

According to an aspect of some embodiments, there is provided an anastomosis device configured to reduce leakage, comprising: a first set of rings sized to be positioned at a first tissue wall; a second set of rings sized to be positioned at a second tissue wall, the second tissue wall being adjacent the first tissue wall; and an element configured to draw the ring sets towards each other; wherein each set of rings comprises an inner ring, an outer ring, and a coupling between the inner ring and the outer ring for aligning the inner and outer rings with respect to each other; wherein when the device is deployed in tissue and the rings sets are drawn towards each other by the element, the inner ring applies a first pressure onto the tissue wall, the first pressure sufficient to gradually form a passage between the first and second tissue walls; and the outer ring applies a second pressure onto the tissue wall, the second pressure applied radially outwardly relative to the first pressure, the second pressure sufficient to reduce leakage in a vicinity of the passage.

In some embodiments, one or both of the inner and outer rings are inflatable.

In some embodiments, the pressure applied by the rings onto the tissue is controlled by inflation pressures.

In some embodiments, a width of the outer ring ranges between 5 mm and 5 cm.

In some embodiments, the rings are collapsible so as to fit within a delivery catheter.

In some embodiments, the element configured to draw the ring sets towards each other comprises an inner construction incorporated in each of the ring sets.

In some embodiments, the inner construction comprises magnetic material incorporated in or mounted on one or both of the inner and outer rings of each set, the magnetic material positioned to induce magnetic attraction between opposing rings.

In some embodiments, the inner construction comprises shape memory material incorporated in one or both of the inner and outer rings of each set, the material shaped and positioned so that deformation of the material changes a level of pressure applied by one or both of the rings onto the tissue.

In some embodiments, the element configured to draw the ring sets towards each other comprises an elongated element sized to extend between the ring sets.

In some embodiments, the elongated element is a stent positionable within the passage.

In some embodiments, the elongated element is a string, wire or cable.

In some embodiments, the elongated element is a needle, the needle comprising a sharp distal end for penetrating the tissue walls.

In some embodiments, the elongated element is tensioned to set at least an initial pulling force between the opposing rings.

In some embodiments, a length of the elongated element defines a maximal distance between the opposing rings.

In some embodiments, the outer ring is configured to apply a radially outwardly decreasing pressure, relative to a center of the formed passage.

In some embodiments, the inner ring, at a cross section, comprises at least one protrusion facing the tissue, the protrusion shaped for cutting the tissue to form the passage.

In some embodiments, the outer ring, at a cross section, comprises raised side edges.

In some embodiments, the coupling between the inner and outer rings comprises one or more bridging elements extending between the inner ring and the outer ring.

In some embodiments, the bridging element is at least 1 mm long for maintaining a radial distance of at least 1 mm between the inner and outer rings when deployed.

In some embodiments, the coupling between the inner and outer rings comprises one or more magnetic elements embedded within and/or mounted on the rings.

In some embodiments, the coupling between the inner and outer rings comprises an adhesive attaching the at least a portion of an outer lining of the inner ring to at least a portion of an inner lining of the outer ring.

In some embodiments, the device comprises one or more inflation tubes for conducting an inflation fluid to the inflatable rings.

In some embodiments, the first set of rings is sized to be placed at a gallbladder wall and wherein the second set of rings is sized to be placed at a duodenum wall, the inner rings configured to form a passage between the gallbladder and duodenum, the passage shaped and sized for allowing gallstones to pass through.

In some embodiments, the device comprises a leakage indicator.

In some embodiments, the indicator comprises a temperature sensor or a PH meter.

In some embodiments, the device comprises one or more pressure sensors positioned at an interface between the tissue and one or both of the rings, the pressure sensors configured to detect an actual pressure applied by the ring onto the tissue.

In some embodiments, the device comprises one or more sensors configured for detecting a level of oxygen saturation of tissue compressed by the device.

In some embodiments, the inner ring further comprises a cutting wire.

In some embodiments, one or both of the inner ring and the outer ring comprise a toroidal shaped balloon.

In some embodiments, a contact surface area of the outer ring with the tissue is larger than a contact surface area of the inner ring with the tissue.

According to an aspect of some embodiments, there is provided a method for leakage-reduced side to side anastomosis, comprising applying a first pressure onto adjacent tissue walls, the pressure sufficient to form a passage between the tissue walls; applying a second pressure onto the tissue walls, the second pressure applied radially outwardly relative to the first pressure, the second pressure sufficient to reduce leakage in a vicinity of the passage.

In some embodiments, the second pressure is lower than the first pressure.

In some embodiments, the second pressure is applied to a tissue surface area of between 1 mm and 5 cm.

In some embodiments, the second pressure is low enough so it substantially does not compromise blood perfusion.

In some embodiments, the first pressure is high enough to cause ischemia but low enough to prevent necrosis of the tissue.

In some embodiments, the adjacent tissue walls comprise a duodenum wall and a gallbladder wall, and wherein the formed passage is sized to allow for gallstones to pass through.

In some embodiments, the adjacent tissue walls comprise walls of different segments of the alimentary tract.

In some embodiments, the method is applied to produce side to side, end to side, or end to end anastomosis between adjacent tissue walls.

In some embodiments, one or both of the first and second pressures vary in time.

In some embodiments, the second pressure varies spatially and is higher at leakage-prone locations.

In some embodiments, the first pressure is between 7-13 Pa.

In some embodiments, the second pressure is between 0.5-3.5 Pa.

According to an aspect of some embodiments, there is provided an anastomosis device configured to reduce leakage, comprising: a set of two rings for positioning over two adjacent tissue walls, each ring comprising at least: a first chamber configured to apply a first pressure onto the tissue wall, the pressure sufficient to form a passage between the first and second tissue walls; and a second chamber configured to apply a second pressure onto the tissue wall, the pressure applied radially outwardly relative to the first pressure, the second pressure sufficient to reduce leakage in a vicinity of the passage.

In some embodiments, the chambers are inflatable.

In some embodiments, the rings comprise one or more valves for regulating the first and second pressures, at least one of the valves configured at a ring wall separating between the first and second chambers.

In some embodiments, the ring further comprises a third chamber configured to apply a third pressure onto the tissue wall, the third pressure lower than the second pressure.

According to an aspect of some embodiments, there is provided a leakage reducing device for use at an anastomosis site, comprising a set of rings for positioning at adjacent tissue walls through which a passage is formed, wherein each of the rings is sized to fit peripherally around an opening of the passage at the tissue wall; the ring configured to apply a pressure onto the tissue, the pressure sufficient to reduce leakage around the opening of the passage.

In some embodiments, the rings are shaped and sized to be used with a tissue stapling device.

According to an aspect of some embodiments, there is provided an anastomosis kit comprising: a flexible shaft defining a proximal end and a distal end; imaging means configured on the shaft; and an anastomosis device coupled to the distal end of the shaft, the device comprising: two sets of rings, each set comprising at least an inner ring configured to apply a first pressure onto the tissue and an outer ring configured to apply a second pressure onto the tissue.

In some embodiments, the imaging means comprise an ultrasonic transducer.

In some embodiments, a distal portion of the shaft onto which the device is mounted is disposable.

In some embodiments, the anastomosis device comprises a leakage indicator.

In some embodiments, the shaft is cannulated and configured to fit on an endoscope.

According to an aspect of some embodiments, there is provided a method for reducing leakage at an anastomosis formed between adjacent tissue walls, comprising identifying leakage at an anastomosis site; deploying a device comprising at least two opposing rings or sections thereof over the adjacent tissue walls; actuating the rings or sections thereof to compress the adjacent tissue walls towards each other to reduce the leakage.

In some embodiments, the method further comprises draining fluid from the anastomosis site.

In some embodiments, the method further comprises, prior to the deploying, grasping and approximating the adjacent tissue walls to each other.

In some embodiments, the actuating is performed from an endo-luminal side of at least one of the tissue walls.

In some embodiments, the deploying comprises advancing one of the rings via the leakage while the second ring remains at an endo-luminal side of one of the tissue walls.

In some embodiments, at least the deploying is performed endoscopically.

In some embodiments, at least the deploying is performed percutaneously, via the abdominal and/or thoracic cavities.

According to an aspect of some embodiments, there is provided an anastomosis device configured to reduce leakage, comprising: a first set of structures shaped and sized to be positioned at a first tissue wall; a second set of structures shaped and sized to be positioned at a second tissue wall, the second tissue wall being adjacent the first tissue wall; and an element configured to draw the sets towards each other; wherein each set of structures comprises an inner substantially closed shape, an outer substantially closed shape surrounding the inner shape, and a coupling element between the inner and outer closed shapes, the coupling element configured to control a ratio between a first pressure applied by the inner closed shape onto the tissue, and a second pressure applied by the outer closed shape onto the tissue.

In some embodiments, the coupling element comprises a wire or cable.

In some embodiments, the coupling element comprises one or more magnets embedded in and/or mounted on the closed shapes.

In some embodiments, a contact surface area of the inner closed shape with the tissue and a contact surface area of the outer closed shape with the tissue are sized to apply a selected level of pressure when a given force is applied to one or both of the closed shapes.

According to an aspect of some embodiments, there is provided a method of implanting an anastomosis device comprising at least two separable portions, comprising approaching a first tissue wall; approaching a second, opposing tissue wall;

approximating the tissue walls to each other; penetrating the first and second tissue walls to produce an initial path through the tissue walls; delivering a first portion of the anastomosis device to be positioned at the first tissue wall; delivering a second portion of the anastomosis device to be positioned at the second tissue wall.

In some embodiments, approaching comprises percutaneously approaching.

In some embodiments, approaching comprises endoscopically approaching.

In some embodiments, the first and second portions of the anastomosis device each comprises a set of rings.

In some embodiments, the method further comprises coupling the first and second portions of the anastomosis device to each other.

In some embodiments, the first tissue wall comprises a gallbladder wall and the second tissue wall comprises a duodenum wall.

According to an aspect of some embodiments, there is provided a clip for adjoining tissue comprising: a main body; a first set of proximally facing hooks attached to a distal end of the main body; a second of distally facing hooks attached to a proximal end of the main body; wherein the hooks are configured to spring outwardly from a collapsed state in which the hooks are substantially aligned with the main body to a deployed state in which the hooks extend sideways relative to the main body.

In some embodiments, the clip is sized to fit within a delivery catheter and the hooks are configured to spring outwardly to the deployed state upon retraction of the catheter.

In some embodiments, the hooks comprise nitinol.

In some embodiments, the clip is shape and sized to be mounted on a needle.

In some embodiments, the clip comprises bioabsorbable material.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments, exemplary methods and/or materials are described below. In case of conflict, the patent specification, including definitions, will control. In addition, the materials, methods, and examples are illustrative only and are not intended to be necessarily limiting.

This summary introduces a selection of concepts in a simplified form that are further described below in the Description of the Figures and the Detailed Description. This summary is not intended to identify key features or essential features of the claimed subject matter, nor is it intended to be used to limit the scope of the claimed subject matter.

BRIEF DESCRIPTION OF THE SEVERAL VIEWS OF THE DRAWINGS

Some embodiments are herein described, by way of example only, with reference to the accompanying drawings. With specific reference now to the drawings in detail, it is stressed that the particulars shown are by way of example and for purposes of illustrative discussion of embodiments. In this regard, the description taken with the drawings makes apparent to those skilled in the art how embodiments may be practiced. In the drawings.

DESCRIPTION OF EMBODIMENTS

Figure 1:
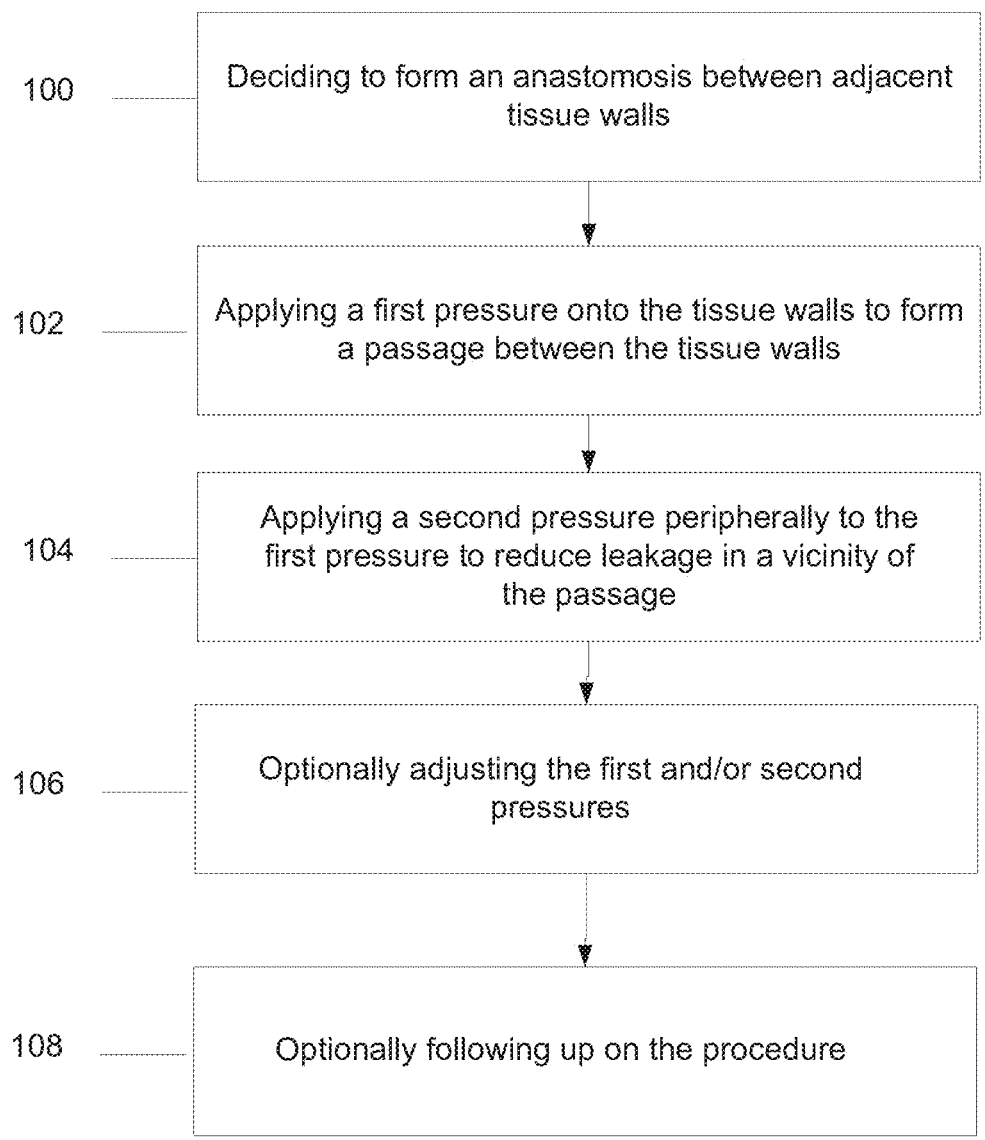
FIG. 1 is a method for leakage-reduced anastomosis, according to some embodiments.

The present invention, in some embodiments thereof, relates to anastomosis, and, more particularly, but not exclusively, to reduced-leakage anastomosis.

A broad aspect of some embodiments relates to forming a passage between opposing tissue walls, such as forming a fistula between the gallbladder and duodenum. In some embodiments, the formed passage provides for the passing of gallstones from the gallbladder to the duodenum. In some embodiments, a passage is created between the other segments and/or organs of the gastrointestinal tract such as the esophagus, stomach, small bowel and/or large bowel.

An aspect of some embodiments relates to reduced-leakage anastomosis.

Some embodiments involve an anastomosis device configured to apply an inner continuous compression force to approximate the peritoneal side of the tissue walls towards each other and form a communicating passage between the two lumens, and further apply an outer, peripheral pressure to reduce leakage around the formed passage.

In some embodiments, the outer pressure approximates the adjacent tissue walls to each other, optionally until some portions of the tissue walls surrounding the passage adhere to each other, while maintaining the tissue viable. A potential advantage of reducing leakage may include reducing a risk of mediastinal, abdominal and/or perineal inflammation and/or other short term or long term pathologies resulting from fluid and/or bowel content leakage, for example leakage into the peritoneal cavity. In some embodiments, leakage is reduced by at least 75%, at least 60%, at least 90% or intermediate, higher or lower percentage relative to an anastomosis in which no pressure other than the passage-producing pressure, namely peripheral pressure, is applied to the adjacent tissue walls. In some embodiments, application of outer pressure to reduce leakage may reduce the need for using staples and/or sutures to attach between at least some portions of the adjacent tissue walls in which the anastomosis is produced.

In some embodiments, the pressure is location-dependent, for example the applied outer pressure decreases as the radial distance from the passage increases. In some embodiments, the pressure is time-dependent, for example the inner pressure is gradually increased over time to form the passage.

In some embodiments, an initial pressure applied by the inner ring is higher than the pressure applied by the one or more outer rings. In some embodiments, pressure applied by the inner ring and/or by the one or more outer rings is reduced over time. Optionally, the applied pressure is reduced as a result of and/or in response to changes in the compressed tissue. Optionally, a gradual reduction in pressure applied to the tissue is more prominent in the inner ring as compared to the one or more outer rings, as the inner ring is configured to apply at least an initial higher pressure suitable for gradually cutting the tissue to form the passage, while the one or more outer rings apply a weaker pressure, which substantially does not comprise the tissue viability, for blocking leakage by compressing the tissue walls against each other.

In some embodiments, the inner pressure is selected to be high enough so as to damage tissue, optionally gradually, to an extent in which the passage can be formed.

Optionally, the inner pressure is effective to restrict blood perfusion to an extent sufficient for gradually cutting through the tissue. In some embodiments, the inner pressure is applied over a few days, (such as 1-5 days) until the passage is formed and/or is enlarged to a selected size (e.g. to have a predefined diameter).

In some embodiments, the outer pressure is low enough so as not to interfere with tissue adherence properties that would allow tissue of a first wall to connect with tissue of an adjacent second wall. Optionally, the outer pressure is sufficient for holding the walls in contact with each other, yet low enough so as not to substantially reduce tissue viability.

Various structures may be employed to provide the dual function of producing a connecting passage between two opposing tissues, and reducing potential leakage from that passage and/or leakage caused as a result of changes in the tissue associated with the passage formation. In some embodiments, the device comprises two sets of double-rings, a first set to be placed at a tissue wall of a first body lumen and a second set to be placed in an opposing, adjacent tissue wall of a second body lumen. In some embodiments, in each set of rings, an inner ring is configured to apply compression force to connect between the tissue walls and form the passage, and an outer ring is configured to apply a pressure sufficient to reduce leakage from and/or around the produced passage.

Optionally, the outer ring is sized to provide a contact area with the tissue that is large enough to ensure the tissue-ring interface is sealed. In some embodiments, the outer ring is large enough to seal one or more spaces that may exist between the adjacent tissue walls. In some embodiments, a contact surface area of the outer ring with the tissue is larger than a contact surface area of the inner ring with the tissue.

Optionally, for the same amount of force applied by and/or to the rings, a higher pressure will be exerted by the inner ring as compared to the outer ring. In some embodiments, the device comprises an element interconnecting the opposing rings. In some embodiments, the element is configured to draw the opposing rings sets towards each other. In some embodiments, the interconnecting element is configured to hold the opposing rings relative to each other, optionally aligning the rings with respect to each other. In some embodiments, the interconnecting element is configured to apply tension on the opposing ring sets, across the tissue walls. In some embodiments, the interconnecting element is configured to apply a pulling force on the opposing inner rings and/or the opposing outer rings to approximate them towards each other.

In some embodiments, the interconnecting element comprises an inner construction incorporated within and/or mounted on the inner and/or outer ring of each set. In some embodiments, the inner construction comprises one or more magnets configured to induce magnetic attraction between opposing rings to draw them towards each other, thereby compressing the tissue walls situated between the rings.

The interconnecting element may be rigid, or, in other embodiments, partially rigid or non-rigid. In some embodiments, the element is elastic. In some embodiments, the element is shapeable, for example can be curved or bent, such as to set a selected distance and/or alignment between the opposing rings.

In some embodiments, the interconnecting element comprises an elongated element that extends across the opposing ring sets. Optionally, the elongated element extends axially (e.g. in a direction substantially perpendicular to the tissue walls) between the centers of the opposing rings. In some embodiments, the elongated element comprises a stent or a barb. In some embodiments, the elongated element is configured to reduce or block leakage from the inner walls of the passage, for example being in the form of a continuous sheath and/or a tubular shaped balloon. Additionally or alternatively, the interconnecting comprises a string, wire or cable long enough to extend between the opposing ring sets. Optionally, the string wire or cable is tensioned to approximate the rings sets towards each other and/or to increase the pressure applied by each of the rings sets onto the respective tissue wall. In some embodiments, tension is applied to the wire by a pulley mechanism, optionally including manual and/or motorized actuation. In some embodiments, the interconnecting element sets an initial pulling force between the opposing rings.

Optionally, the interconnecting element is tensioned and/or shortened to approximate the rings towards each other. In some embodiments, the initial attraction produced by the element causes the opposing rings (inner and/or outer rings) to apply an initial pressure onto the tissue walls, even before the rings are inflated and/or otherwise actuated (e.g. by magnetic and/or shape memory actuation) to compress the tissue.

In some embodiments, the interconnecting element defines a maximal distance between the opposing rings. Additionally or alternatively, the interconnecting element defines a minimal distance between the rings, for example being rigid enough to prevent the rings from moving closer to each other.

In some embodiments, the interconnecting element is effective to apply a pulling force onto the inner rings only. Optionally, each of the inner rings is coupled to its respective outer ring via an attachment suitable for transferring the pulling force so that the outer rings will be indirectly pulled towards each other as a result of pulling the inner rings.

In some embodiments, a coupling between the inner and outer ring comprises a direct attachment, for example the inner lining of the outer ring is attached to the outer lining of the inner ring, for example via adhesive means. Alternatively, in some embodiments, the outer ring is spaced apart from the inner ring. Optionally, the spaced apart outer ring is coupled to the inner ring via a bridging element. In some embodiments, the bridging element is rigid enough to transfer a pulling force initially applied, for example, to the inner rings, to the outer rings. Additionally or alternatively, a coupling between the inner and outer rings is achieved by use of magnetic elements mounted on and/or embedded within the rings.

Optionally, the magnetic elements are positioned to align and/or set a distance between the inner and outer rings.

In some embodiments, controlled pressure is applied by the rings onto the tissue. In some embodiments, the rings are inflatable, and the amount of pressure applied to the tissue by the rings is controlled by the inflation pressure. Additionally or alternatively, the rings comprise shape memory material (such as nitinol) and are deformed to apply and/or change (e.g. reduce or remove) the selected pressure(s).

Additionally or alternatively, magnetic means are used and the strength of the magnetic attraction is selected and/or modified to control the pressure applied by the rings onto the tissue.

Some embodiments include a set of two rings, in which a single ring is positioned on either side of the tissue, the ring configured to apply various and/or varying pressures for example by comprising multiple, separately inflatable chambers.

Alternatively, some embodiments include configurations in which three or more rings are positioned on either side of the tissue.

In some embodiments, a peripheral ring set is placed about an anastomosis device configured to form the passage. Such device may include, for example, a stapler, a cutter, a wire, optionally electrically conductive, configured for cutting and/or coagulating tissue, and/or other devices suitable for producing a passage between the adjacent tissue walls and/or for cutting through tissue.

In some embodiments, a cutting wire is embedded within and/or on an inner ring of a device for example as described hereinabove. Optionally, the cutting wire is used with or instead of the inner applied pressure to form the passage.

In some embodiments, the peripheral ring is inflatable. Additionally or alternatively, the peripheral ring is actuated by magnetic means. Additionally or alternatively, the peripheral ring is actuated by shape memory means.

In some embodiments, the passage is formed (e.g. by applying a "tissue cutting" pressure, employing a cutting wire and/or other actions suitable to form the passage) only after at least some leakage protection is provided by the peripheral rings, for example after the peripheral rings applied enough pressure to cause serosal surfaces of the adjacent tissue walls to at least partially adhere to each other.

In some embodiments, application of a "tissue cutting" pressure is initiated upon implantation of the device. Alternatively, application of the "tissue cutting" pressure is initiated only at a later stage, for example hours or days following implantation.

Various surgical approaches may be performed for implanting devices for example as described herein. In some embodiments, the anastomosis device is implanted endoscopically, for example introduced through a natural orifice of the alimentary tract, and/or via an access point created during a laparotomy or laparoscopy. Alternatively, the anastomosis device is implanted percutaneously.

An aspect of some embodiments relates to implantation of an anastomosis device in a combined surgical approach. Optionally, each tissue wall is approached from a different body lumen, for example the gallbladder wall is reached from the gallbladder lumen and the duodenum wall is reached from the duodenum lumen. In an example, the duodenum wall is approached endoscopically, and the gallbladder wall is approached percutaneously.

In some embodiments, the anastomosis device comprises at least two portions configured to be introduced into the body independently of one another, for example a first portion comprising a first set of rings for positioning at a first tissue wall, and second portion comprising a second set of rings for positioning at a second tissue wall.

Optionally, implantation is performed under image guidance, for example using automated and/or robotic imaging modalities, comprising, for example, an ultrasound transducer, a fluorography imaging device, and/or other scanning and/or imaging modalities. In some embodiments, the anastomosis device is mounted on an endoscope or a laparoscope and delivered to the target site. Additionally or alternatively, the anastomosis device is mounted on or delivered through a shaft comprising imaging means (e.g. using video and/or ultrasound) for advancing the device to the target site. The shaft may be flexible or rigid.

In some embodiments, the device is delivered to target site in a deflated or collapsed condition. Optionally, the device is delivered via a tube (such as via an endoscope working channel, via a catheter, via a stent, in an over the scope method and/or other delivery methods). In some embodiments, the device is delivered over a guide wire. In some embodiments, the device is delivered over a tube or a stent.

In some embodiments, during implantation of the device, an initial path is created through the tissues to provide for deploying the device over the two tissue walls. Optionally, the initial path is produced by a needle, a catheter tip, and/or other thin tools suitable for penetrating the tissues. In some embodiments, the larger passage produced by the anastomosis device hours or days after implantation is formed around the initial path. Optionally, the initial path defines the center of the later formed passage.

In some embodiments, an anastomosis device configured to form a passage of a certain shape and/or size (e.g. diameter) is selected. Optionally, a diameter of a substantially cylindrical passage is between, for example, 1 mm and 7 cm, 10 mm and 1 cm, 3 cm and 5 cm, 1 cm and 3 cm or intermediate, larger or smaller diameters. In the example of gallbladder-duodenum and/or gallbladder stomach anastomosis, a shape and/or size of the passage may be selected in accordance with a shape and/or size and/or amount of gallstones that need to be removed, for example evacuated from the gallbladder to the lumen of the gastrointestinal tract.

In some embodiments, the anastomosis device comprises bio-absorbable materials. Optionally, the device is naturally absorbed over time, for example after 2 weeks, after 6 weeks, after 9 weeks, after 1 month, after 3 months, or intermediate, longer or shorter periods of time.

In some embodiments, the device comprises one or more sensors. In some embodiments, the device comprises one or more sensors configured for detecting a current tissue condition, for example an oximeter for detecting oxygen saturation in the compressed tissue. In some embodiments, the device comprises one more sensors for detecting leakage, including, for example, chemically activated sensors (e.g. a PH sensor) which react in the presence of a leaking fluid, such as bile, pancreatic fluid, and/or in the presence of HCl. In some embodiments, one or more pressure sensors are incorporated within one or more of the rings. Optionally, the pressure sensors are positioned at the ring-tissue interface and are configured to detect an actual pressure currently applied by the ring onto the tissue.

In some embodiments, a set of rings configured for compressing tissue to reduce or prevent leakage is placed about a previously formed anastomosis.

Optionally, a leaking site is detected, and the ring set is deployed across the leaking opening to hold and pressurize the tissue towards each other to an extent sufficient for reducing or fully blocking the leakage.

In some embodiments, a draining tube extends from the rings for clearing away fluid from the leaking site, for example to outside the body.

An aspect of some embodiments relates to approximating tissue walls to each other. In some embodiments, opposing tissue walls are moved closer to each other in preparation for deploying the anastomosis device at the leakage site. In some embodiments, an initial path is produced through the approximated tissue walls, for example by penetrating the walls (e.g. using a needle).

In some embodiments, a tissue adjoining device such as a clip is placed to approximate and/or to maintain hold of the tissue walls to each other, for example to facilitate deployment of the anastomosis device. In some embodiments a clip comprising a plurality of hooks is provided, the hooks being shaped and directed to obtain hold of one or both of the tissue walls. In some embodiments, the hooks are configured to spring outwardly from a collapsed configuration to a deployable configuration, for example upon retraction of a delivery catheter. In an exemplary use, a first set of hooks is deployed at the gallbladder wall and the clip is pulled back, thereby pulling the gallbladder wall closer to the duodenum wall. Optionally, a second set of hooks is then deployed at the duodenum wall for holding the walls against each other.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

Referring now to the drawings, FIG. 1 is a flowchart of a method for reduced-leakage anastomosis, according to some embodiments.

In some embodiments, a decision is made (for example by a physician such as a gastroenterologist, a surgeon, an interventional radiologist and/or other clinical personnel) to form an anastomosis between adjacent tissue walls (100). Surgical intervention by performing anastomosis is used, for example, for treating digestive tract related conditions, such as gallstones. In some cases, the decision is made during hospitalization and/or during a surgical procedure and/or in an ambulatory setting and/or in a clinic.

In some embodiments, a passage is created between adjacent body lumens, for example between the gallbladder and duodenum, between the gallbladder and stomach, between the stomach and the small intestine, between the esophagus and the stomach or small intestine, between different segments of the stomach, between the stomach and a cyst or a pseudocyst in the peritoneal cavity or in the retroperitoneum, and/or between any two segments of the gastrointestinal tract. In some embodiments, the passage is created by applying a first pressure onto opposing tissue walls of the adjacent body lumens (102).

In some embodiments, the applied first pressure is high enough to approximate the tissue walls to each other and to compress the tissues until a passage is formed. In some embodiments, continuous compression force is applied. Optionally, the first pressure increases gradually over time until the passage between the two lumens is formed. In some cases, a constant pressure is applied to the tissue, but due to weakening and/or deformation of the tissue in response to the applied pressure, the pressure acting on the tissue effectively decreases. In some embodiments, the first pressure is applied for a time period of between 1 hour and 3 weeks, 1 hour and 3 hours, 1 day and 6 days, 5 hours and 2 days, or intermediate, longer or shorter time periods. In some embodiments, the first pressure is selected to be high enough so as to damage tissue to an extent in which the passage can be formed, for example high enough to cause local inflammation of the tissue that may promote adherence of the opposing walls to each other (such as due to fibrotic changes). Additionally or alternatively, the first pressure is selected to be high enough so as to restrict blood perfusion in the compressed tissue, optionally within the area surrounded by the inner ring. In some embodiments, the first pressure is selected to be low enough to avoid premature formation of the passage, for example to provide for anastomosing of outer tissue first (e.g. of tissue located radially outwardly to the tissue region in which blood perfusion was restricted).

In some embodiments, a cross sectional area of the formed passage is selected to be large enough to allow passing of biological matter through. The biological matter may include, for example fluid such as bile and/or blood and/or mucus and/or other fluid, and/or solid material such as gallstones and/or fecal matter. In some embodiments, non-biological material such as medication is passed through.

In some embodiments, the passage is shaped and/or sized to allow for passing of medical instruments through, for example an endoscope (e.g. for performing gallstone extraction and/or tissue debridement and/or hemostatic procedures and/or collecting a tissue biopsy and/or ablating tissue and/or any other producers). The cross sectional profile may be circular, elliptic, arbitrary and/or any other profiles.

In some embodiments, a stent and/or a barb and/or any other support element are placed at the passage between the adjacent body lumens, optionally extending along a central axis of the passage. Optionally, the support element is configured to maintain the formed passage open. Support elements of varying cross sectional profiles and/or sizes (e.g. diameters) may be used, optionally according to the need.

In some embodiments, a second pressure is applied peripherally to the first pressure to reduce leakage in a vicinity of the formed passage (104).

Leakage may be caused by of one or more of surgical failure, reduced blood perfusion at the anastomosis, tension on the tissue walls, infection, certain medical treatments such as chemotherapy or steroids, a nutritional condition of the patient and/or others. The type of fluid(s) at risk of leaking may depend on the anastomosis location, and may include, for example, bowel content which may contain inflammatory fluids such as gastric acid, bile, pancreatic secretions and/or feces.

In some embodiments, the second pressure is lower than the first pressure. In some embodiments, the second pressure is selected to be high enough to reduce leakage from the formed passage. In some embodiments, the second outer pressure is selected to be low enough so as to avoid ischemia and/or tissue necrosis which may interfere with the adherence properties of the tissue. In some embodiments, tissue viability is maintained. A potential advantage of maintaining tissue viability may include improving and/or expediting tissue adherence, and/or promoting tissue healing post-operation.

In some embodiments, the second pressure is applied by an element which is shaped to be positioned around the passage and to contact a tissue area large enough so as to seal the area peripherally to the passage and reduce or prevent leakage.

In some embodiments, the second pressure is applied simultaneously to the first pressure.

In some embodiments, the second pressure is applied for a time period of between 7-12 days. Optionally, within that time period, the second pressure is sufficient to cause serosal surfaces of the adjacent tissue walls adhere to each other. In some embodiments, the second pressure is applied for a longer period of time.

Optionally, the time period is selected in accordance with a medical condition of the patient, for example in patients exhibiting impaired nutritional status, a low level of albumin, patients prescribed with medication that is known to affect the healing process, a catabolic state of the patient and/or other conditions, the second pressure is applied for a longer period of time, for example 14 days, 20 days, 40 days, 50 days or intermediate longer or shorter time periods. In some embodiments, the second pressure varies spatially. In an example, the second pressure decreases in a radially outward direction relative to the passage. In another example, the second pressure is higher at leakage-prone locations (for example locations in which the tissue is tensioned).

In some embodiments, the first and/or second pressure is adjusted (106). In some embodiments, control over the applied pressure is provided by controlling inflation pressure, in embodiments in which the device comprises inflatable balloon rings. In some embodiments, control over the inflation pressure is achieved by use of one or more valves such as one way valves, for example providing for gradual decompressing. Additionally or alternatively, one or more materials suitable for providing a predefined and/or controlled decompression are used. Additionally or alternatively, control over the applied pressure is provided using magnetic means. For example, in some embodiments magnetic elements are incorporated in one or both the inner and outer ring of a double ring and/or other multiple ring (e.g. triple ring) device, for example embedded at tissue facing surfaces of the rings, and magnetic attraction between opposing rings is utilized to align and/or compress the adjacent tissue walls against each other, optionally until a passage is formed. Optionally, the ring is comprised of magnetic material. Additionally or alternatively, control over the applied pressure is provided using shape memory means. For example, in some embodiments shape memory material such as Nitinol is used, and the shape memory effect is utilized to apply (or instead, cease) pressure onto the tissue, for example in response to a temperature change. Additionally or alternatively, control over the applied pressure is provided by using absorbable materials, which expand when absorbed with a fluid to apply pressure onto the tissue.

In some embodiments, control over the applied pressure is provided using extracorporeal and/or intracorporeal magnetic and/or electrical induction.

Additionally or alternatively, control over the applied pressure is provided using manual and/or automatically activated motors. In some embodiments, one or more motors are incorporated within the device and/or in a guiding catheter and/or endoscope. Optionally, the one or more motors are operably attached to the one or more rings of the device to control application of pressure. In some embodiments, the one or more motors are remotely controlled, for example via tubing extending from the device to outside the body and/or by wireless control. In some embodiments, the motors are configured to actuate inflation and/or deflation of the device's rings.

In some embodiments, the pressure is modified with the aid of an endoscope, for example using an endoscope to adjust a valve (e.g. at least partially opening and/or closing the valve).

In some embodiments, the anastomosis device is pre-set to apply selected pressure(s), for example using one or more of the above control means. Additionally or alternatively, the pressures are adjusted on demand, for example adjusted manually from outside the body, such as by modifying an inflation level.

In some embodiments, pressure values are selected in accordance with results of prior studies. Additionally or alternatively, pressure values are selected in accordance with data sensed in real time, for example using one or more sensors configured to indicate a current pressure applied to the tissue and/or tissue oxygenation condition and/or a tissue perfusion condition and/or combinations thereof.

Figure 7A:
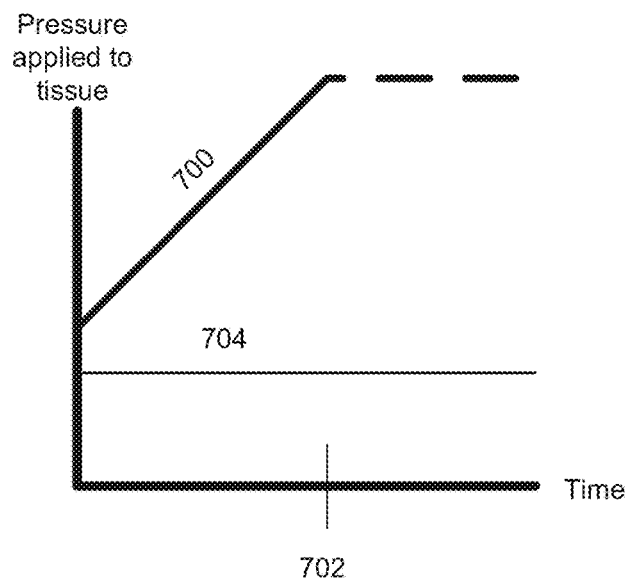
FIGS. 7A-D are graphical representations of time-dependent pressures applied by an anastomosis device, according to some embodiments.
Figure 7B:
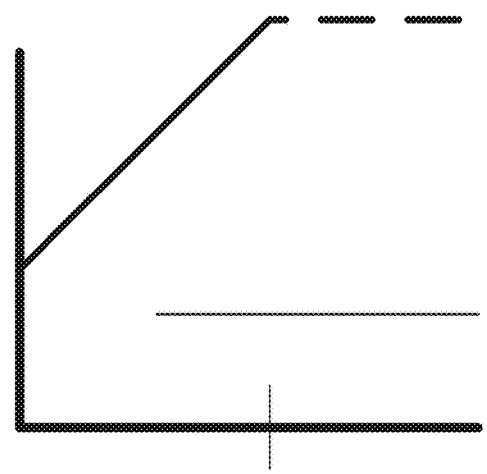
Figure 7C:
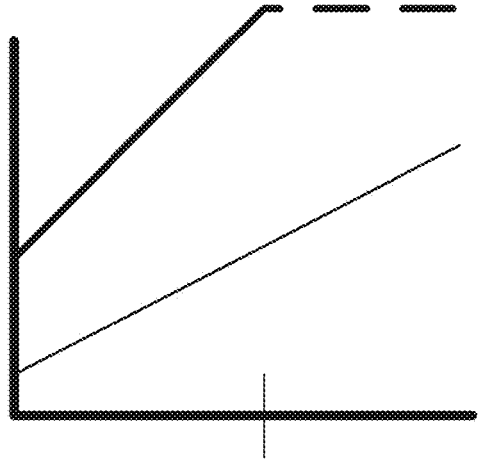
Figure 7D:
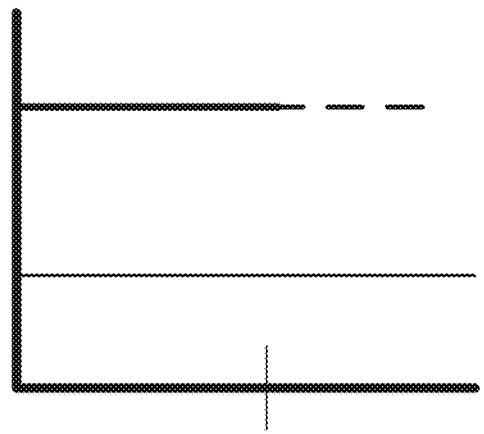
Figure 8A:
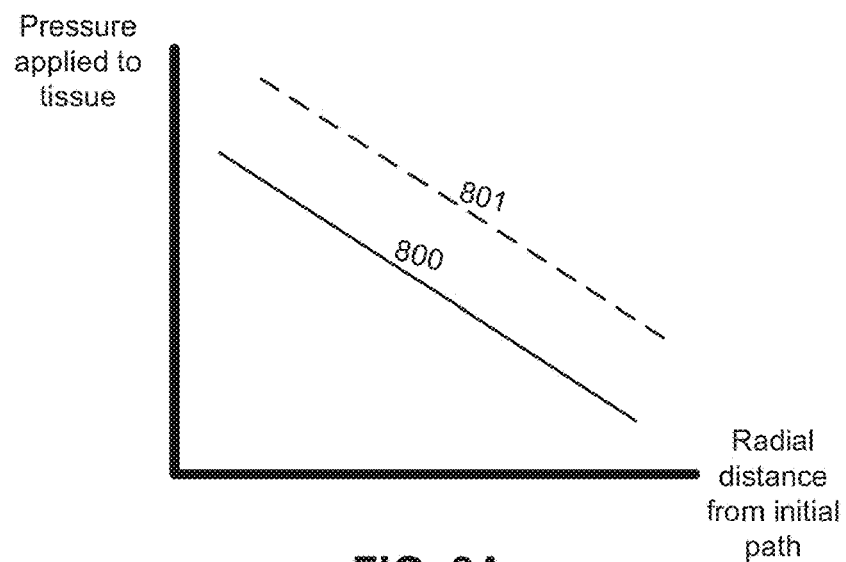
FIGS. 8A-C are graphical representations of distance-dependent pressures applied by an anastomosis device, according to some embodiments.
Figure 8B:
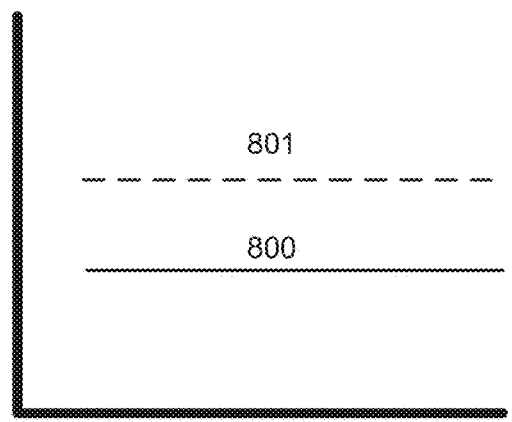
Figure 8C:
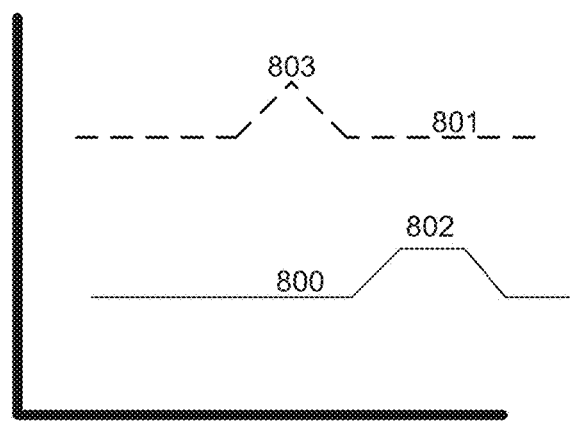

In some embodiments, the first and/or second pressure levels are distance-dependent, for example as shown in FIGS. 8A-C below. In some embodiments, the first and/or second pressures are time-dependent, for example as shown in FIGS. 7A-D below.

In some embodiments, the physician follows up on the procedure (108).

Optionally, an effectiveness of the treatment is assessed, for example whether evacuation of gallstones through the passage was achieved. In some embodiments, a condition of the tissues in which the anastomosis was formed is assessed. In some embodiments, the physician checks for leakage at the anastomosis site. Optionally, leakage is identified by one or more of imaging means (for example via fluoroscopy, using contrast material and/or via a CT scan showing excessive fluid and/or extra-luminal contrast material in the peritoneal cavity) and/or by identifying clinical signs such as pain, high pulsation rate, fever, reduced urinary output, reduced blood pressure and/or others.

In some embodiments, follow up is performed using indications provided by one or more sensors configured on and/or within the device and/or sensors placed in tissue adjacent the device, for example including pressure sensors, oximeters, chemical sensors and/or others.

In some embodiments, the produced passage remains open over time.

Alternatively, for example if a relatively narrow passage was formed, the passage may naturally close (e.g. due to build-up of fibrotic tissue in the passage).

In some cases, the risk of leakage decreases over time. Optionally, immediately after formation of the passage the risk is highest, and after a few days (such as 4, 6, 8, 10 days) the risk of leakage is no longer significant.

Figure 2A:
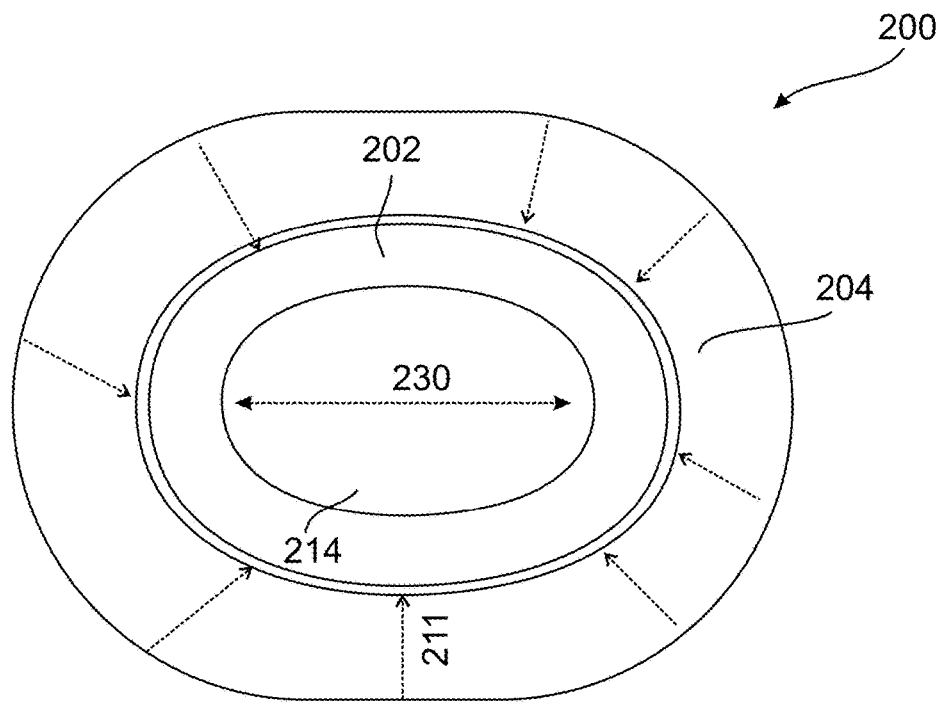
FIGS. 2A-B schematically illustrate a double-ring device for reduced-leakage anastomosis, according to some embodiments.
Figure 2B:
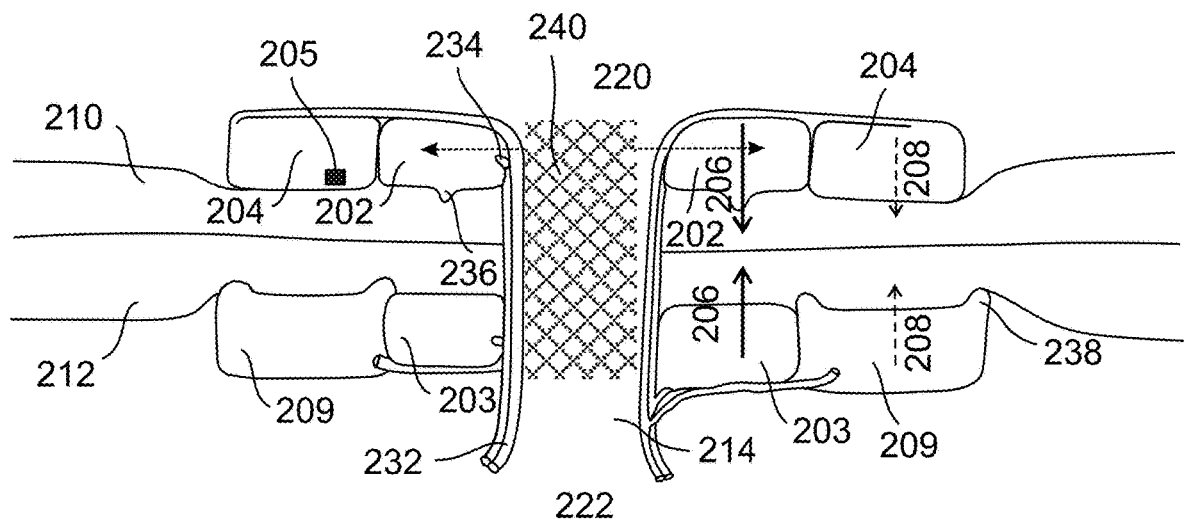

FIGS. 2A-B schematically illustrate a double-ring device for reduced-leakage anastomosis, according to some embodiments.

In some embodiments, device 200 comprises two sets of rings, each set including a first inner ring 202 and a second outer ring 204.

FIG. 2A is a view of the device as seen from within one of the body lumens 220, 222 (shown in FIG. 2B) being connected by the anastomosis. FIG. 2B is a cross section of the device showing adjacent tissue walls 210 and 212 sandwiched between the opposing ring sets, and the formed passage 214.

In some embodiments, inner rings 202 and 203 are configured to apply a first pressure 206 onto the tissue (see FIG. 2B). In some embodiments, pressure 206 is applied towards the opposing inner ring, in an axial direction corresponding with the direction of the passage. In some embodiments, a pressure level in rings 202 and 203 is similar. Alternatively, the rings comprise different pressure levels. Optionally, different pressure levels are applied to produce a curved impression on the tissue surface, forming a concave/convex interface between the two inner rings.

In some embodiments, pressure 206 is high enough to compress the adjacent tissues against each other and, eventually, to cut through the tissues to form the passage. Optionally, pressure 206 ranges between, for example, 7-20 Pa, such as 10 Pa, 13 Pa, 17 Pa or intermediate, higher or lower values. Optionally, pressure 206 is applied gradually, for example a relatively low pressure is applied at first to approximate the tissue walls towards each other, and then a higher pressure is initiate forming of the passage.

In some embodiments, outer rings 204 and 209 are configured to apply a second pressure 208 peripherally to the first pressure 206 (see FIG. 2B). In some embodiments, pressure 208 is applied onto the tissue (i.e. in an axial direction parallel to the passage), towards the opposing outer ring.

In some embodiments, radial pressure 211 is applied by outer ring 204 and/or outer ring 209 onto the inner ring (i.e. in a radially inwards direction). Optionally, pressure 211 is lower than pressure 208.

In some embodiments, pressure 208 is sufficient to reduce fluid leakage at the anastomosis, for example by sealing a tissue region surrounding the openings of passage 214 to lumens 220 and 222. Optionally, pressure 208 is sufficient to push tissue regions that surround the opening of the passage (at each of opposing tissue walls) towards each other. Optionally, pressure 208 is applied continuously for a time period which is long enough to promote natural adherence of the opposing tissue walls to each other, for example tissue of at the periphery of the inner rings.

In some cases, the time period is long enough to provide for healing of the adhered tissue. In some embodiments, pressure 208 is applied over a time period ranging between, for example, 1 hour and 1 week, 1 day and 10 days, 1 week and two weeks, for example 5 hours, 2 days, 4 days, 1 week, 10 days, or intermediate, longer or shorter time periods. Optionally, pressure 208 is applied to widen passage 214 which was formed by the inner rings, only after establishing a peripheral healing process by gradually compressing the tissue walls against each other gradually. A potential of a pressure low enough so that it does not substantially compromise blood perfusion, at least until peripheral tissues adhered to each other, may include promoting healing of the tissue surrounding the passage, potentially providing for growth of new tissue at the anastomosis site. Optionally, pressure 208 ranges between, for example, 0.5-3.5 Pa, for example 1 Pa, 2 Pa, 2.5 Pa or intermediate, higher or lower pressure levels.

In some embodiments, outer ring 204 (and/or outer ring 209) is sized to contact a surface area of the tissue which is large enough to reduce leakage, for example having a width 228 of between 1 mm and 6 cm, 5 mm and 2 cm, 1 cm and 3 cm or intermediate, larger or smaller width.

In some embodiments, an inner diameter 230 of inner ring 202 is selected according the need, to form a passage of a similar diameter. Optionally, inner diameter 230 ranges between, for example, 1 mm and 10 cm, such as 5 mm, 1 cm, 3 cm, 5 cm or intermediate, larger or smaller diameter.

It is noted that in some embodiments the device may comprise inner and/or outer elements that are not necessarily circular, for example elliptic elements. In some embodiments, the elements are shaped to define a substantially closed shape or frame.

In some embodiments, the substantially closed shape is defined by a plurality of contact points in which pressure is applied to the tissue. Optionally, contact points of the outer closed shape are closer to each other than contact points of the inner close shape, so as to ensure sealing of the tissue surrounding the passage.

It is also noted that the formed passage may be of various cross sectional profiles and/or cross sectional areas.

In some embodiments, one or both of the rings are inflatable. Optionally, one or more inflation tubes such as inflation tube 232 extend to a port 234 of the ring (in this example ring 204) to conduct fluid, such as air, water, saline and/or other fluid suitable for inflating the ring. Optionally, the pressure level of the ring is controlled by inflation pressures. Some embodiments comprise a safety valve configured to prevent over-inflation, for example by releasing excessive fluid (e.g. air) from the device.

In some embodiments, tube 232 extends from the ring through a catheter (e.g. an endoscope working channel and/or through any other conduit extending to the anastomosis site), providing for inflating and/or modifying inflation of the ring from externally to the body.

In some embodiments, the inner and/or outer ring comprise one or more sensors 205. In some embodiments, sensor 205 is a pressure sensor. Optionally, sensor 205 is positioned at the ring-tissue interface and is configured to measure an actual pressure applied by the ring onto the tissue. Additionally or alternatively, a pressure sensor is positioned at the interface between the adjacent tissue walls. Optionally, the sensor is coupled to a linking element extending between the opposing ring sets, such as stent 240 further described herein.

In some embodiments, sensor 205 is configured to indicate tissue oxygen saturation. In some embodiments, sensor 205 is configured to detect a level of blood perfusion.

In some embodiments, sensor 205 is a chemically activated sensor. Optionally, sensor 205 is configured to detect leakage, for example being a PH sensor, enzyme sensor, bile sensor and/or other sensor suitable for detecting leakage. In some embodiments, sensor 205 is a color changing sensor, e.g. a liquid crystal sensor.

Optionally, during and/or following implantation, the color changing sensor is viewed under imaging.

In some embodiments, one or both of the rings define a toroidal configuration when inflated. Optionally, one or both of the rings are shaped to affect the tissue being contacted by the ring. In an example, inner ring 202 comprises a central protrusion 236 extending in the axial direction which defines a cutting edge which may facilitate forming the passage through the tissue. Optionally, central protrusion 236 is configured to apply increased pressure at a localized point, for example a pressure high enough to cause local ischemia for forming the passage between the tissue walls. Additionally or alternatively, opposing inner ring 203 comprises an axially extending protrusion (not shown).

In some embodiments, the inner ring is shaped to define (at a cross section) a narrowing suitable to apply localized pressure onto the tissue is order to produce a cutting action.

In some embodiments, outer ring 209 or 204 comprises raised side protrusions 238 which may enhance blocking of leakage. Optionally, the opposing inner ring comprises raised complementary protrusions (not shown). In some embodiments, one or both of the outer rings comprise multiple dentate axially extending protrusions, for example aligned along a circumference of the ring. Optionally, the protrusions of the opposing rings (204 and 209) are complementary to each other. A potential advantage of complementary circumferential protrusions may include enhancing sealing at the interface between the two rings, for reducing leakage. In some embodiments, the outer ring is wide-spread and/or comprises extensions (at a cross section) suitable to enlarge contact with the tissue. Optionally, under a given force applied to the ring sets, the inner ring applies a higher localized pressure onto the tissue while the outer ring applies a lower, more spread out pressure onto the surrounding tissue.

In some embodiments, the rings comprise or are formed of one or more bio-absorbable materials. Optionally, the rings are absorbed in the body after a time period of, for example, 3 days, 1 week, 3 weeks, 2 months, 6 months, 12 months or intermediate, longer or shorter time periods.

In some embodiments, the inner and outer rings are coupled to each other via one or more connecting lines or structures (not shown herein). Optionally, the connecting structures comprise bioabsorbable material. Optionally, the connecting structures extend from one or more circumferential locations of the inner ring to the outer ring, bridging between the rings. In some embodiments, the rings are connected in a manner in which changes in the inner ring (e.g. dislodgement, absorbance in tissue) do not affect the outer ring and/or vice versa. A potential advantage of maintaining at least some separation between the inner and outer rings may include providing for leakage protection by the outer ring even in cases in which the inner ring slipped, migrated, was moved and/or absorbed. In some embodiments, the connecting structure is configured to transfer and/or divide and/or otherwise set the amount of force applied by the inner ring and/or by the outer ring onto the tissue.

Optionally, the connecting structure controls a ratio of the pressures applied by the inner and outer rings, for example by being rigid enough to transfer force from one ring to another. In some embodiments, the connecting structure aligns the inner and outer rings with respect to each other. Optionally, the connecting structure sets a maximal and/or minimal distance between inner and outer rings, such as between the outer perimeter of the inner ring and the inner perimeter of the outer ring.

In some embodiments, a stent 240, a tube and/or barb and/or any other device suitable to support the passage walls and maintain the passage open is implanted in passage 214. In some embodiments, stent 240 is self-expanding. In some embodiments, the stent is a covered stent, for example comprising a coating of leakage proof material such as Tephlon and/or Gortex (PTFE). Alternatively, the stent is non-covered. In some embodiments, the stent comprises a bioabsorbable material.

Additionally or alternatively, the stent is retrieved after a period of time, for example by means of endoscopy.

In some embodiments, the stent is coupled to the opposing ring sets (e.g. coupled to the inner rings), acting as a linking element between the opposing ring sets. Optionally, the stent is configured to apply tension so as to draw the opposing rings towards each other (and thereby press on the tissue situated in between).

In some embodiments, the stent comprises a cylindrical profile. Alternatively, the stent comprises an hourglass curvature and/or other profiles suitable for use within the passage.

In some embodiments, the stent comprises one or more markings, optionally radiopaque. In some embodiments, the stent and the anastomosis device comprise corresponding markings for assisting in a positioning (e.g. aligning) of the stent relative to the anastomosis device.

Figure 3A:
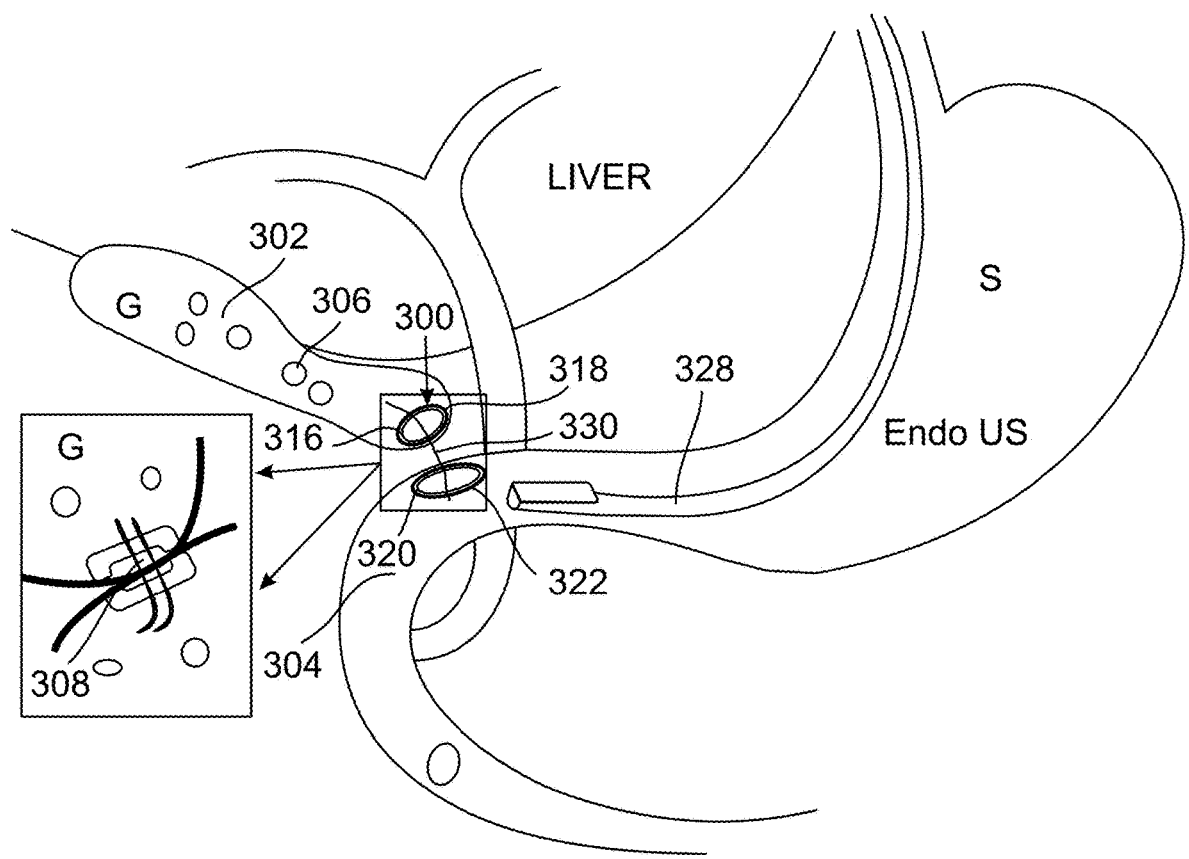
FIGS. 3A-B schematically illustrate anastomosis between the gallbladder and duodenum, optionally for the passing of gallstones through, according to some embodiments.
Figure 3B:
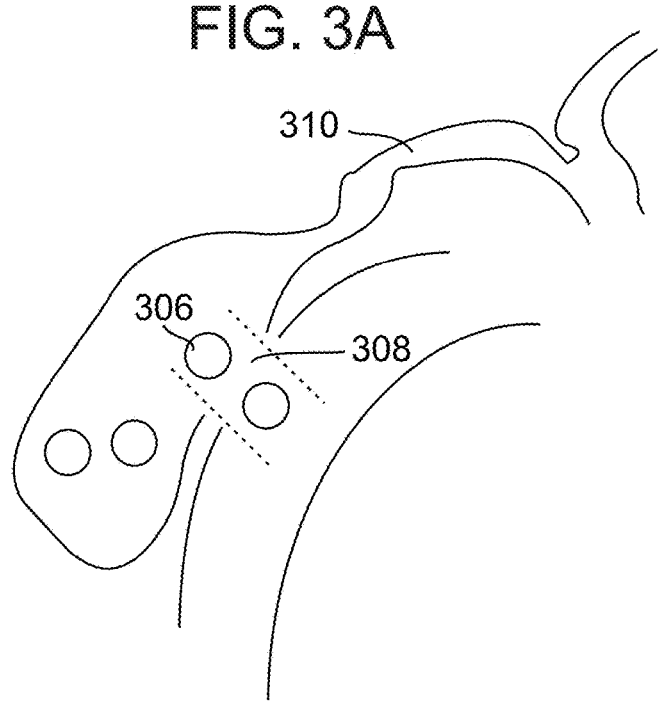

FIGS. 3A-B schematically illustrate anastomosis between the gallbladder and duodenum, optionally for the passing of gallstones through, according to some embodiments. FIG. 3A illustrates the anatomical positioning of the device, according to some embodiments. FIG. 3B illustrates the passing of gallstones through the formed passage, according to some embodiments. In some embodiments, an anastomosis device 300 is implanted to form a passage 308 between the lumens of the gallbladder 302 and duodenum 304 (cholecystoenterostomy) for clearing gallstones 306 from the gallbladder by allowing and/or actively causing (e.g. using endoscopical means) the gallstones to flow through the passage and into the duodenum, from which the gallstones are naturally removed by the digestive system.

Commonly, gallstones formed in the gallbladder pass into the cystic duct 310 (see FIG. 3B), where they may block the gallbladder and cause complications such as inflammation (cholecystitis) and/or biliary colic. If the gallstones pass through the cystic duct and further obstruct the main bile duct, complications such as obstructive jaundice, ascending cholangitis and/or acute pancreatitis may be caused. In some embodiments, passage 308 defines a bypass which prevents or reduces the amount of gallstones passing from the gallbladder to the cystic duct 310. In some embodiments, the formed passage may reduce or prevent symptoms of obstruction of the gallbladder such as biliary colic and/or cholecystitis. Optionally, the formed passage may reduce or prevent stasis of bile in the gallbladder, thereby reducing a risk of further formation of gallstones.

In some embodiments, a first set of rings of device 300 (including an inner ring 316 and an outer ring 318, according to some embodiments) is positioned at the inner side of the gallbladder wall, and a second set of rings of device 300 (including an inner ring 320 and an outer ring 322) is positioned at the inner side of the adjacent duodenum wall. In some embodiments, a tensioning element such as a string 330 extends across the opposing ring sets. Optionally, string 330 is configured to be tensioned so as to draw the rings sets (e.g. the inner rings and/or outer rings of the opposing sets) towards each other.

In some embodiments, compression pressure applied by inner rings 316 and 320 approximates the tissue walls and opens passage 308 that connects between the gallbladder and duodenum lumens. Gallstones 306 may spontaneously flow through the formed passage, and/or, in some embodiments, may be actively caused to pass through the passage. For example, large gallstones (such as over 2 cm in diameter, over 3 cm in diameter, over 4 cm in diameter or intermediate, larger or smaller sizes) may not pass spontaneously, and may be actively caused to pass through the passage using, for example, endoscopic tools. Optionally, intervention is performed only after the anastomosis is fully established and the tissue has healed.

In some cases, gallstones that passed to the bowel are eliminated through the feces.

In some embodiments, outer rings 318 and 322 are positioned to around inner rings 316 and 320 respectively. Optionally, the outer rings are configured to reduce leakage of duodenal and gallbladder content to the surrounding peritoneal cavity.

In some embodiments, device 300 is implanted in an elective procedure.

In some embodiments, endoscopic imaging means such as endoscopic ultrasound (EUS) 328 are used during the procedure for delivering the device to the selected anatomical implantation site and/or for imaging during operation.

It is noted that in a known human pathology (gallstone ileus) a cholecysto-duodenal fistula is created naturally by a very large gallstone which leans against the tissue and forms such opening. In some cases, the large gallstone passes to the duodenum. In some cases, the opening between the gallbladder and duodenum remains even after the large gallstone is surgically removed from the body, and substantially does not any complications. This pathology may provide proof of feasibility to the above described principles of the procedure.

It is noted that any area of the gallbladder wall may be selected as the site for anastomosis. Similarly, in the case of cholecysto-alimentary tract anastomosis, any segment of the alimentary tract including the stomach, duodenum and the small bowel may be selected as the site for anastomosis.

Other types of anastomosis in which the device may be used may include cholecysto-gastrostomy, cholecysto-duodenostomy, cholecysto-intestinal, cholecysto-jejunal, or cholecysto-ileal anastomosis.

It is noted that the example described herein presents side-to-side anastomosis, but methods and/or devices for example as described herein may be used for end-to-side as well as end-to-end anastomosis and/or side to end anastomosis. Further, in some embodiments the device (or portions thereof, such as the outer ring or a segment thereof) may be implanted at a previously formed anastomosis site, for example as referred to hereinbelow in FIGS. 15A-C and 17A-B.

Figure 4A:
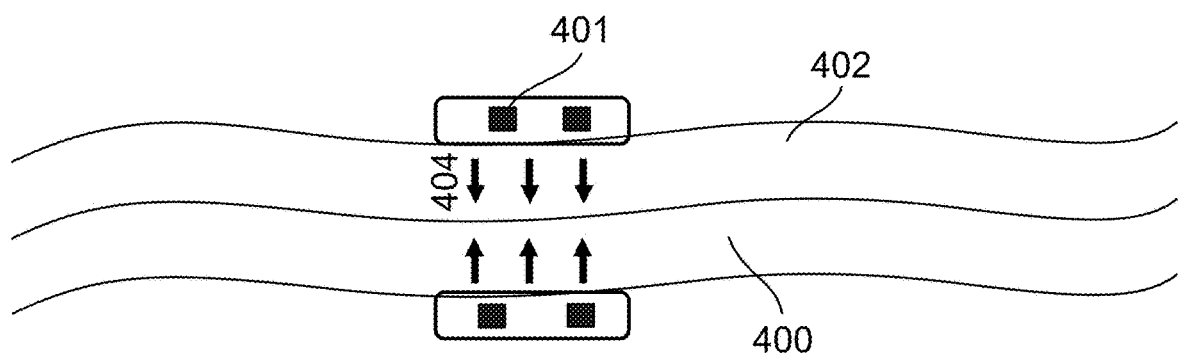
FIGS. 4A-C schematically illustrate a device comprising magnetic and/or shape memory material, according to some embodiments.
Figure 4B:
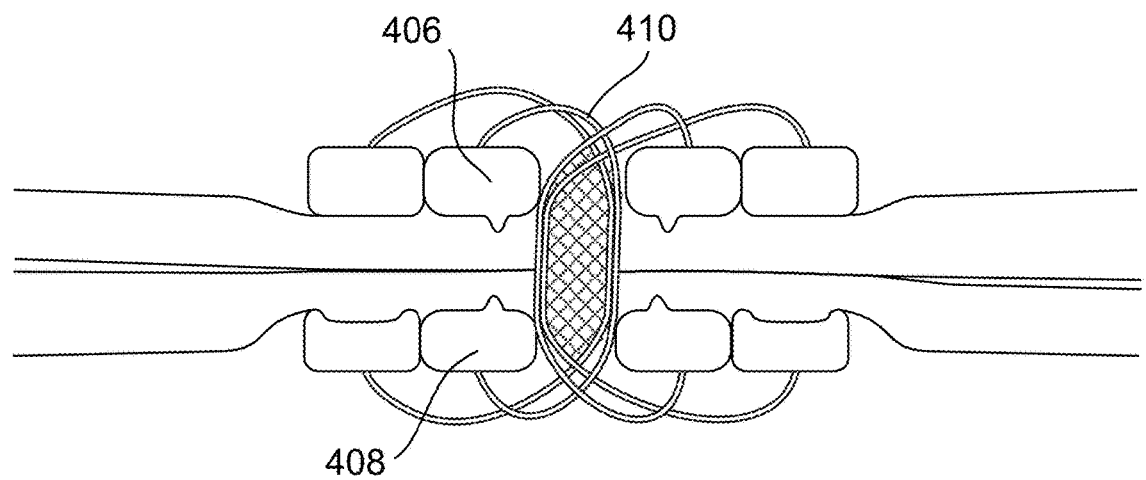
Figure 4C:
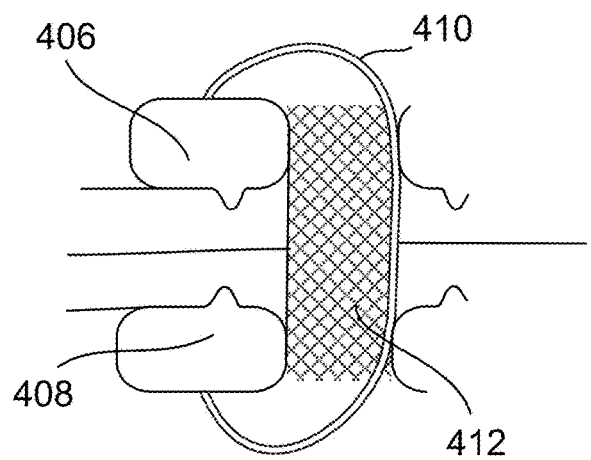

FIGS. 4A-C schematically illustrate a device comprising magnetic and/or shape memory material, according to some embodiments.

In some embodiments, magnetic attraction is utilized for applying and/or modifying of the pressure applied by the inner and/or outer ring onto the tissue. Optionally, magnets 401 are placed on and/or within rings that are positioned over the adjacent tissue walls 400 and 402 (for example as shown in FIG. 4A), and magnetic attraction 404 between the rings gradually draws the rings towards each other, compressing the tissue trapped between the rings. Optionally, the rings are formed of non-magnetic material, and magnetic attraction is affected only by the use of magnetic elements embedded in the rings and/or mounted on the ring surface.

In some embodiments, a size and/or shape of the magnets is selected in accordance with the selected pressure to be applied by the rings. In an example, the inner rings comprise larger and/or stronger magnets and/or a higher number of magnets relative to the outer rings to provide for applying a stronger compression force on the trapped tissue than the pressure applied by the outer rings. In some embodiments, the compression force applied by the magnets and/or by shape memory alloy of the outer ring is configured to approximate the tissue walls and adhere the walls to each other. Optionally, the applied force is low enough so as not to compromise blood perfusion and oxygenation of the compressed tissue.

Additionally or alternatively to the use of a magnetic field, in some embodiments, shape memory material is used for applying and/or modifying of the pressure applied by the inner and/or outer ring onto the tissue. Optionally, the shape memory material deforms in response to a temperature change, for example a temperature change occurring when the rings are inserted into the body. Examples of shape memory material may include one or more of: nickel-titanium alloys (Nitinol), copper-aluminum-nickel, copper-zinc-aluminum, and iron-manganese-silicon alloys.

In an example, the inner rings comprise a Nitinol wire that extends axially between the lumens, across the passage. Optionally, the wire is an extension of a stent positioned in the passage. In some embodiments, the wire exerts a first pressure when in room temperature, and, when inserted into the body, (i.e. to a temperature of 37 degrees Celsius) applies a higher pressure, for example a pressure of between 7-13 Pa, sufficient for gradually perforating a passage through the tissue. In some embodiments, for example in the above described setup, the outer ring is configured to apply a pressure lower than the inner ring, for example a pressure between 1-1.5 Pa.

In some embodiments, in a device comprising shape memory material, the opposing rings (i.e. both inner rings and/or both outer rings) are inherently connected or a formed of a single body of material, configured to apply pressure from both sides of the anastomosis. In some embodiments, during implantation, the shape memory device is forced into a substantially straight delivery tube. Optionally, when the device is placed at the site for anastomosis, it is released from the delivery tube and allowed to gain its predefined shape. In some embodiments, the predefined shape comprises opposing inner rings formed of an integral body of shape memory material, and opposing outer rings formed of the same integral body of material as the inner rings and/or made of a different body of material. Optionally, each set of rings (i.e. inner, outer) is configured to compress the adjacent tissue walls at a different, optionally pre-set pressure.

FIGS. 4B and 4C illustrate a device comprising inflatable rings and one or more shape memory elements, according to some embodiments. In some embodiments, opposing rings such as 406 and 408 (see FIG. 4C, which shows only a single set of opposing rings of the device shown in FIG. 4B, for clarity) are connected to each other via one or more wires 410 comprising shape memory material, such as a nitinol wire. Optionally, wire 410 is configured to exert a pulling force on the opposing rings to approximate the rings towards each other, thereby compressing the tissue. In some embodiments, the pulling force varies in time and/or magnitude. In some embodiments, wire 410 is an extension of a stent 412 that is positioned to extend axially along the passage.

Figure 5:
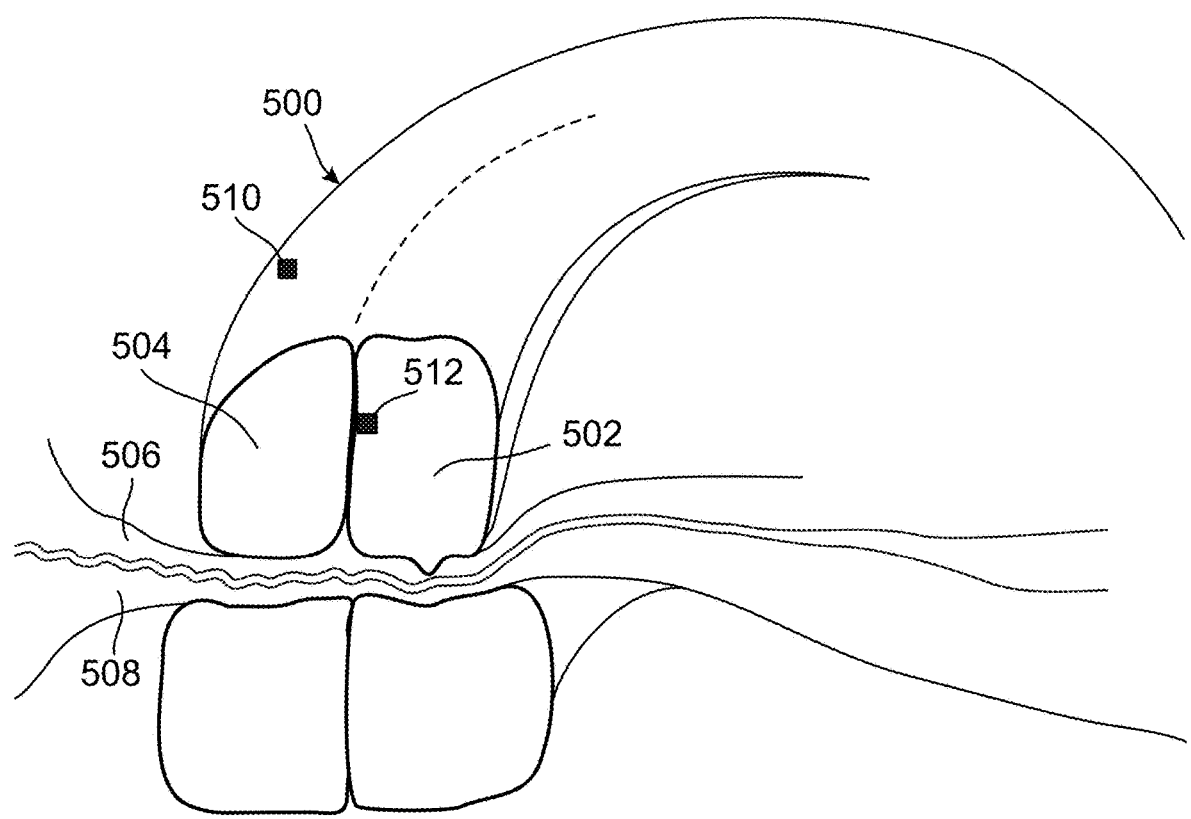
FIG. 5 schematically illustrates a chambered ring device for reduced-leakage anastomosis, according to some embodiments.

FIG. 5 schematically illustrates a chambered ring device for reduced-leakage anastomosis, according to some embodiments. In some embodiments, device 500 comprises a single ring which includes two or more inner chambers, optionally having a circular cross section profile, such as inner chamber 502 and outer chamber 504. In some embodiments, the chambers are separately inflatable. In some embodiments, inner chamber 502 is inflated to apply a first pressure onto the tissue, the pressure being high enough to form a passage between tissue walls 506 and 508, and outer chamber 504 is inflated to apply a second, optionally lower pressure onto the tissue, the second pressure being sufficient to reduce leakage around the passage.

In some embodiments, the ring comprises a plurality of chambers, for example 3, 5, 8, 10 or intermediate, larger or smaller number of chambers. In some embodiments, the ring is configured to apply radially-changing pressure, for example pressure that gradually increases towards the center of the ring. In some embodiments, the ring comprises one or more valves for inflation and/or regulation of the pressure.

Optionally, one or more valves such as 510 are configured on the outer walls of the ring. Additionally or alternatively, one or more valves such as 512 are configured at inner walls of the ring, for example at a wall separating between the chambers.

Figure 6A:
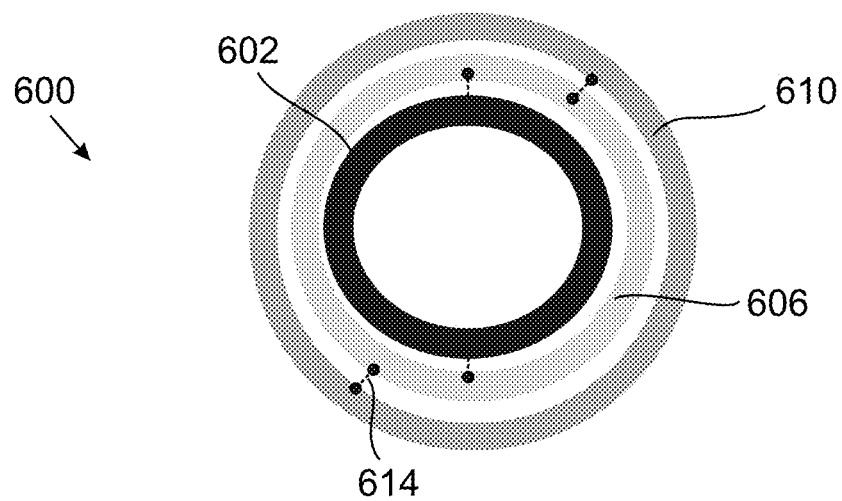
FIGS. 6A-B schematically illustrate a triple-ring device for reduced-leakage anastomosis, according to some embodiments.
Figure 6B:
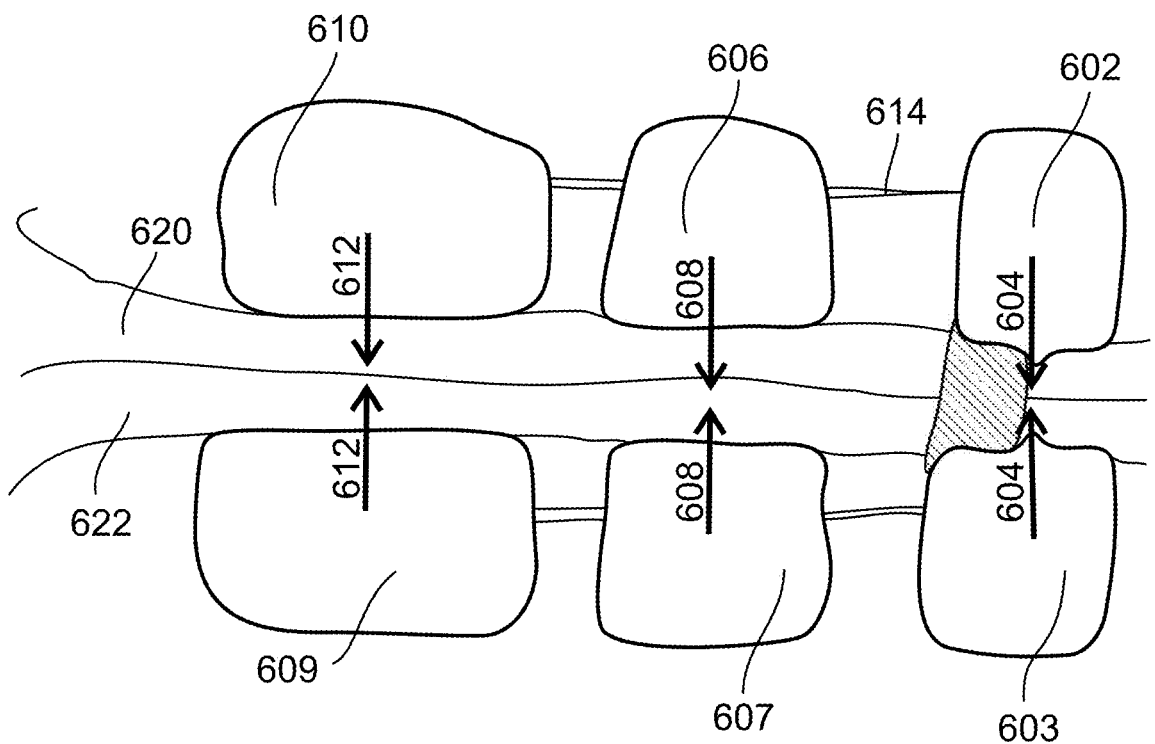

FIGS. 6A-B schematically illustrate a triple-ring device for reduced-leakage anastomosis, according to some embodiments. FIG. 6A shows a schematic cross section of the triple-ring device as viewed from one of the lumens, and FIG. 6B is a cross section of the device showing adjacent tissue walls 620 and 622 sandwiched between the opposing ring sets.

In some embodiments, device 600 comprises triple-ring sets. In an example, innermost rings 602 and 603 are configured to apply a pressure 604 high enough to form the passage; middle rings 606 and 607 are configured to apply an intermediate pressure 608; and outermost rings 610 and 609 are configured to apply a lower pressure 612. It is noted that the pressure applied by a set of opposing rings may be similar, or, in some embodiments, different.

In some embodiments, the rings comprise various widths. Optionally, the ring width increases in a radially outward direction relative to the formed passage such that innermost ring 602 is the narrowest and outermost ring 610 is the widest. (For clarity, the description refers to a set of rings on one side of the tissue, but may apply to the opposing ring set as well). A potential advantage of multiple rings having a radially increasing width with respect to each other may include contacting a larger surface area of the tissue to reduce the risk of leakage.

In some embodiments, the rings (of each of the sets) are configured to be positioned at a distance from each other. Optionally, one or more bridging elements 614 connects between adjacent rings.

In some embodiments, bridging element 614 comprises a string, wire or cable, optionally comprising a bioabsorbable material. In some embodiments, bridging element 614 is elastic. A potential advantage of an elastic element may include allowing at least some relative movement between the rings, for example due to movement of the inner ring once the passage has formed.

Alternatively, bridging element 614 is rigid. Optionally, bridging element 614 is configured to restrict at least some relative movement between the rings.

FIGS. 7A-D are graphical representations of time-dependent pressures applied by an anastomosis device, according to some embodiments.

In some embodiments, the first and/or second pressures are applied over time.

Optionally, the pressures are applied simultaneously. Alternatively, the pressures overlap for only a predetermined period of time. Alternatively, the pressures are applied one after another.

In some embodiments, the first and/or second pressure rise over time.

Alternatively, the first and/or second pressure remain constant. Alternatively, the first and/or second pressure descend over time.

FIGS. 7A-D illustrate various examples of time dependent pressures, according to some embodiments.

In the example shown in FIG. 7A, the first (inner) pressure 700 which is configured to form the passage gradually rises, and at 702, for example when the passage is fully defined (for example referring to the case of gallstone treatment, at 702 the formed passage is already large enough to allow passing of gallstones through), and optionally there is no longer viable tissue between the opposing inner rings, pressure 700 either remains constant or is ceased. The second (outer) pressure 704 in this example is lower than the first pressure, and remains constant.

In the example shown in FIG. 7B, the first pressure 700 is similar to the described above in FIG. 7A, but the second pressure 704 is initiated only at a later time point. In an example, the second pressure in initiated 1 or 2 days before the passage is fully defined. In some embodiments, the second pressure is initiated in response to measurements obtained via one or more pressure sensors or other sensors configured to detect a current condition of the tissue.

In the example shown in FIG. 7C, the first pressure 700 is similar to the described above in FIG. 4A, but the second pressure 704 gradually increases over time. Optionally, the second pressure 704 remains low enough so as to provide for blood perfusion.

In the example shown in FIG. 7D, both of the pressures are constant.

Optionally, first pressure 700 is ceased at 702.

In some embodiments, passage formation 702 occurs after a time period of between 2-7 days, such as 3 days, 4 days, 6 days or intermediate, longer or shorter time ranges. Optionally, the second pressure continues for a time period of between 2-4 seeks, such as 2.5 weeks, 3 weeks after formation of the passage.

It is noted that the schemes shown herein are only exemplary and that the first and/or second pressures may be applied according to other schemes and/or combinations thereof.

FIGS. 8A-C are graphical representations of distance-dependent pressures applied by an anastomosis device, according to some embodiments. In some embodiments, the first and/or second pressure vary as a function of the radial distance from the formed passage, such as relative to a center of the passage. In some embodiments, the pressures vary spatially with respect to an initial path that was created through the tissues when implanting the device, for example a path created by a needle and/or other thin device suitable for penetrating the tissues. In some embodiments, the passage is formed around the initial path, such that the initial path becomes the center of the larger passage produced by the device In some embodiments, the first pressure is applied a radial distance of between 0-3 cm from the initial path, such as 0.5 cm, 1 cm, 2 cm or intermediate, longer or shorter distances from the initial path.

In some embodiments, the second pressure is applied to a circumferential tissue region which extends from the initial path to a radial distance of at least 0.5 cm, at least 3 cm, at least 7 cm, at least 9 cm or intermediate, longer or shorter distances from the initial path.

In FIGS. 8A-8C, the first pressure (passage producing pressure) is represented by the dashed lines; the second pressure (leakage reducing pressure) is represented by the continuous lines.

In the example shown in FIG. 8A, first pressure 801 and second pressure 800 decrease as the distance from the initial path increases.

In the example shown in FIG. 8B, both pressures remain constant as the distance from the initial path increases.

In the example shown in FIG. 8C, first pressure 801 varies with respect to the distance, for example comprising a rise 803 at a selected radial distance from the initial path. A potential advantage of one or more rises in the first pressure may include accelerating cutting through the tissue to form the passage.

In some embodiments, as also shown for example in FIG. 8C, second pressure 800 varies with respect to the distance, for example rising at a leakage prone tissue location 802 and descending or remaining constant at locations that are less prone to leakage. In some embodiments, leakage prone locations are locations in which one or both of the tissue walls have a lower thickness relative to other tissue regions. Optionally, the leakage prone locations include locations in which blood perfusion was compromised, for example locations that are closer to the passage.

Optionally, the leakage prone locations include locations in which the tissue is highly tensioned.

In some embodiments, leakage prone locations are detected using imaging means, such as ultrasound. Additionally or alternatively, leakage prone locations are detected using one or more sensors incorporated within and/or on the surface of the ring device.

It is noted that the schemes shown herein are only exemplary and that the first and/or second pressures may be applied according to other schemes and/or combinations thereof.

Figure 9A:
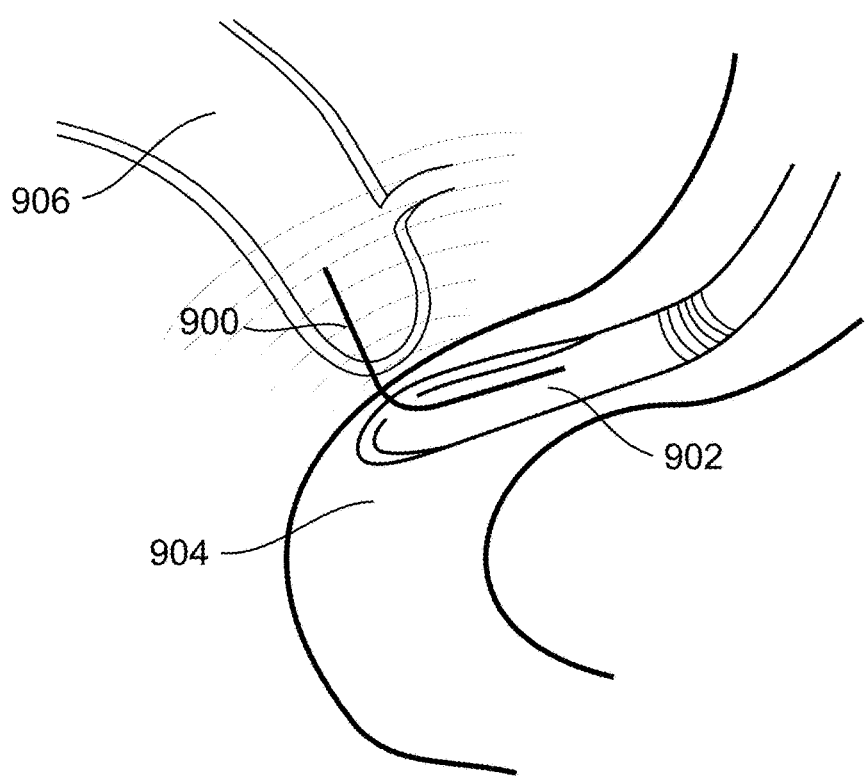
FIGS. 9A-C illustrate a first approach for implanting an anastomosis device to connect between the gallbladder and duodenum, according to some embodiments.
Figure 9B:
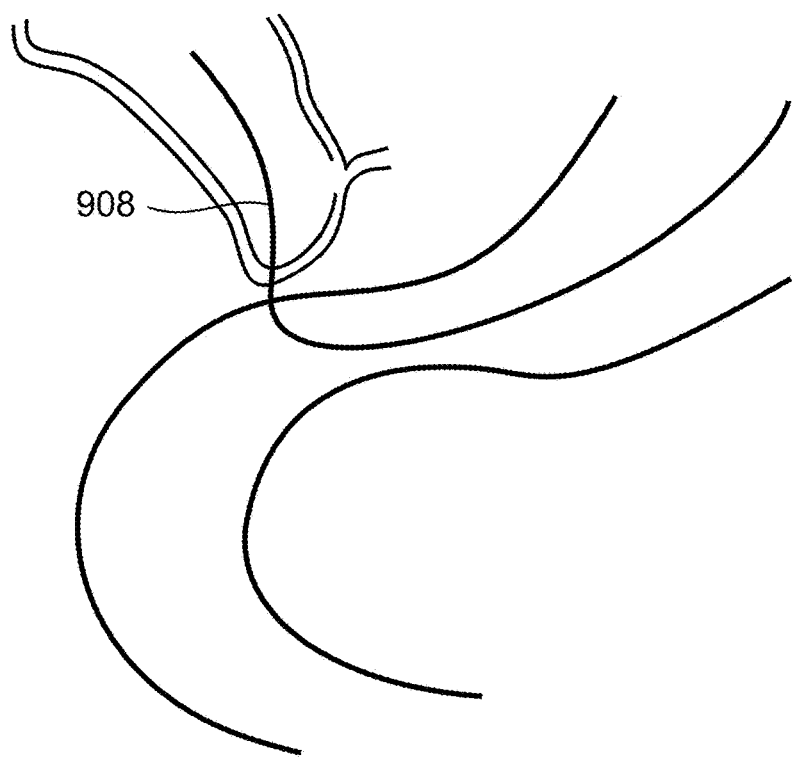
Figure 9C:
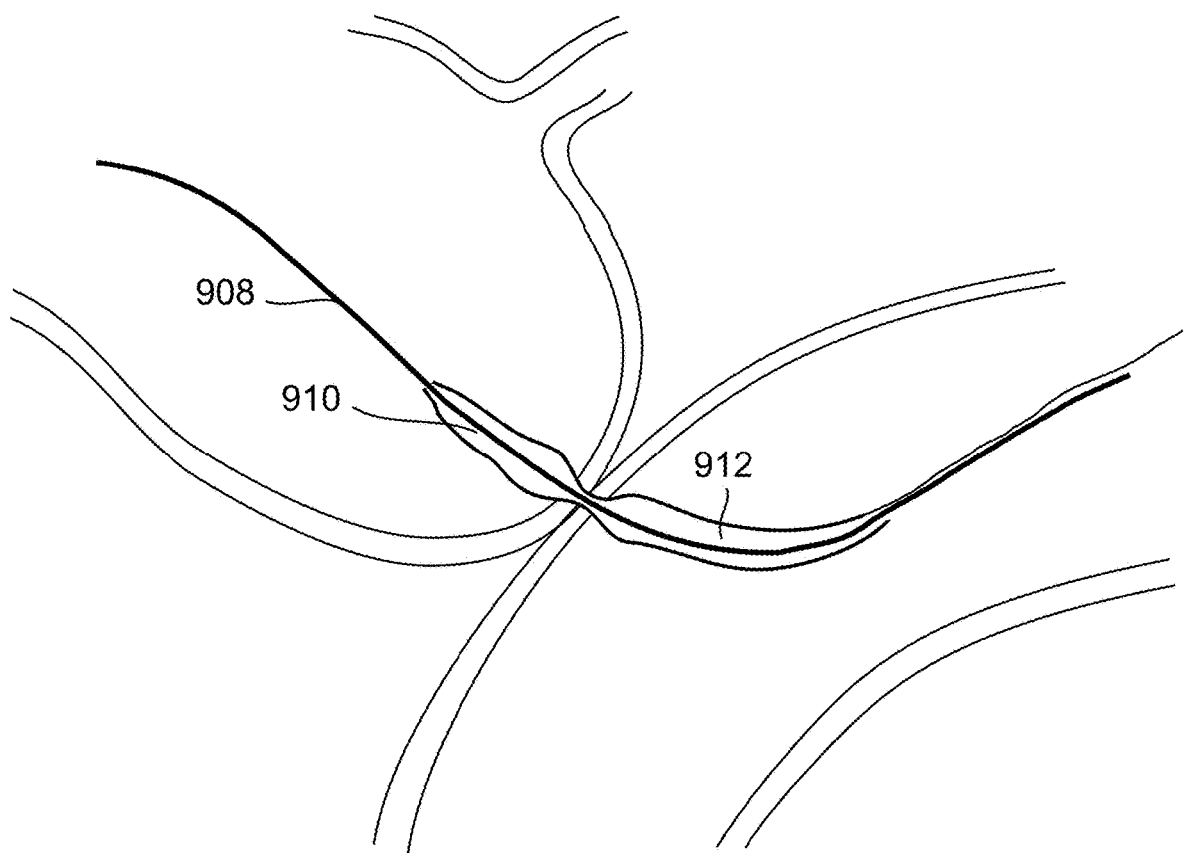

FIGS. 9A-C illustrate a first approach for implanting an anastomosis device to connect between the gallbladder and duodenum, according to some embodiments.

In some embodiments, the anastomosis device is implanted via an endoscopic approach. In some embodiments, as shown for example in FIG. 9A, a needle 900 is inserted under imaging guidance (such as extracorporeal and/or intracorporeal ultrasound guidance, CT and/or MRI) via an endoscope 902 and is advanced from the duodenum 904 to the gallbladder 906, penetrating the adjacent tissue walls.

A flexible guide 908 (e.g. a wire) is then introduced via needle 900 through the duodenum to the lumen of the gallbladder, as shown for example in FIG. 9B. Once guide 908 is introduced into the gallbladder, the anastomosis device is delivered over the guide to the adjacent walls of the gallbladder and duodenum, as shown for example in FIG. 9C. In this example, the anastomosis device comprises two sets of inflatable rings: set 910 is delivered distally to the gallbladder wall (in a deflated condition), and set 912 is delivered proximally to the duodenum wall (optionally still in a deflated condition). In some embodiments, set 910 is inflated before set 912 (not shown herein). A potential advantage of inflating set 910 before set 912 may include approximating the gallbladder wall to the opposing duodenum wall, potentially facilitating maneuvering of the inflated device from the duodenal side. Alternatively, both sets are inflated simultaneously. Alternatively, set 912 is inflated first.

Optionally, fluid is delivered to inflate the ring sets, for example via one or more inflation tubes extending to the inner and/or outer ring.

In some embodiments, a final position of the inflated device is verified, for example using imaging means, such as fluoroscopy and/or ultrasound means.

In some embodiments, ring sets 910 and 912 are coupled to each other.

Optionally, the sets are coupled to each other only during insertion to the body, and are separated from each other when placed at the tissue walls. Optionally, the sets are attached to a central shaft (not shown herein). In some embodiments, the shaft is configured to axially expand, for example so as to allow positioning of the ring sets over the adjacent tissue walls. In some embodiments, the shaft comprises a stent-like structure. Optionally, the shaft comprises and/or is formed of a shape memory alloy. In some embodiments, the shaft is coated by a thin layer of material, such as PTFE and/or Teflon.

In some embodiments, the shaft comprises one more extensions, for example configured at the proximal and/or distal ends of the shaft, for receiving each of the ring sets. Optionally, an extension comprises ring-shaped wires on which the inflatable rings are placed. Optionally, the ring shaped wires are rigid enough to maintain a configuration of the inflatable device.

In some embodiments, in which the rings are inflated with fluid, the fluid may include different color dyes for each of the rings (e.g. a dye of a first color for inflating the inner ring, a dye of a second color for inflating the outer ring). Optionally, the colored fluid may provide an indication to the patient and/or physician in the case of accidental puncture and/or planned deflation of a ring.

In an example, the colored fluid may be passed on by the urine and provide an indication of the device condition without invasive intervention.

Figure 10:
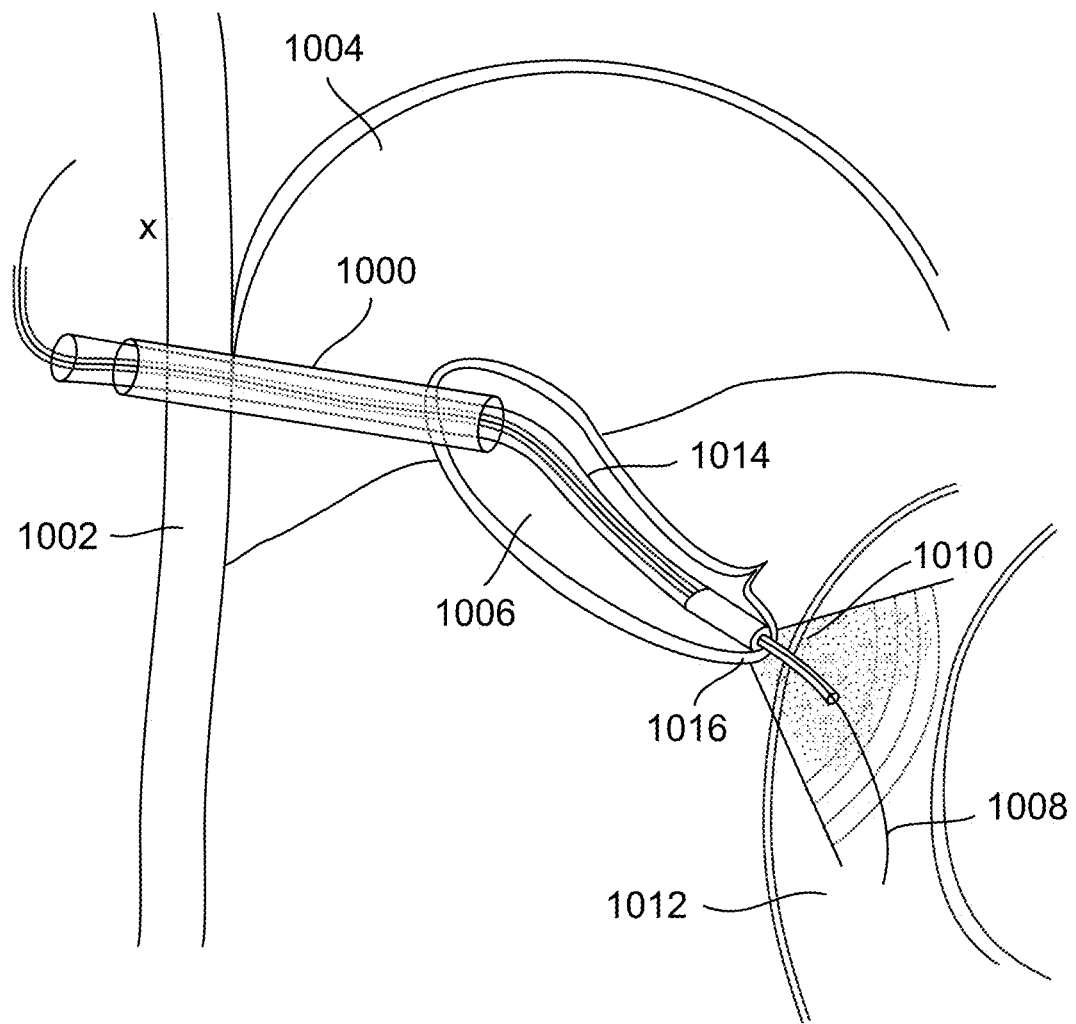
FIG. 10 illustrates a second approach for implanting an anastomosis device to connect between the gallbladder and duodenum, according to some embodiments.

FIG. 10 illustrates a second approach for implanting an anastomosis device to connect between the gallbladder and duodenum, according to some embodiments.

In some embodiments, the anastomosis device is implanted via a percutaneous approach. In some embodiments, a catheter 1000 (for example a transhepatic cholecystostomy tube is inserted through skin 1002, via liver 1004 and into the lumen of gallbladder 1006. In some embodiments, a flexible guide 1008 is passed through catheter 1000 to penetrate gallbladder wall 1016 and adjacent duodenum wall 1010, entering the duodenum lumen 1012. In some embodiments, guide 1008 is delivered through a working channel of an ultrasound probe 1014, used for imaging. Additionally or alternatively, in some embodiments, extracorporeal imaging means such as CT, MRI, and/or ultrasound are used.

It is noted that in some embodiments guide 1008 is delivered through any other endoscopic tool, for example a flexible, semi-flexible or rigid tool. Optionally, the tool is equipped with imaging means such as video and/or ultrasound.

In some embodiments, the anastomosis device (not shown herein) is delivered over guide 1008 to the implantation site.

Figure 11:
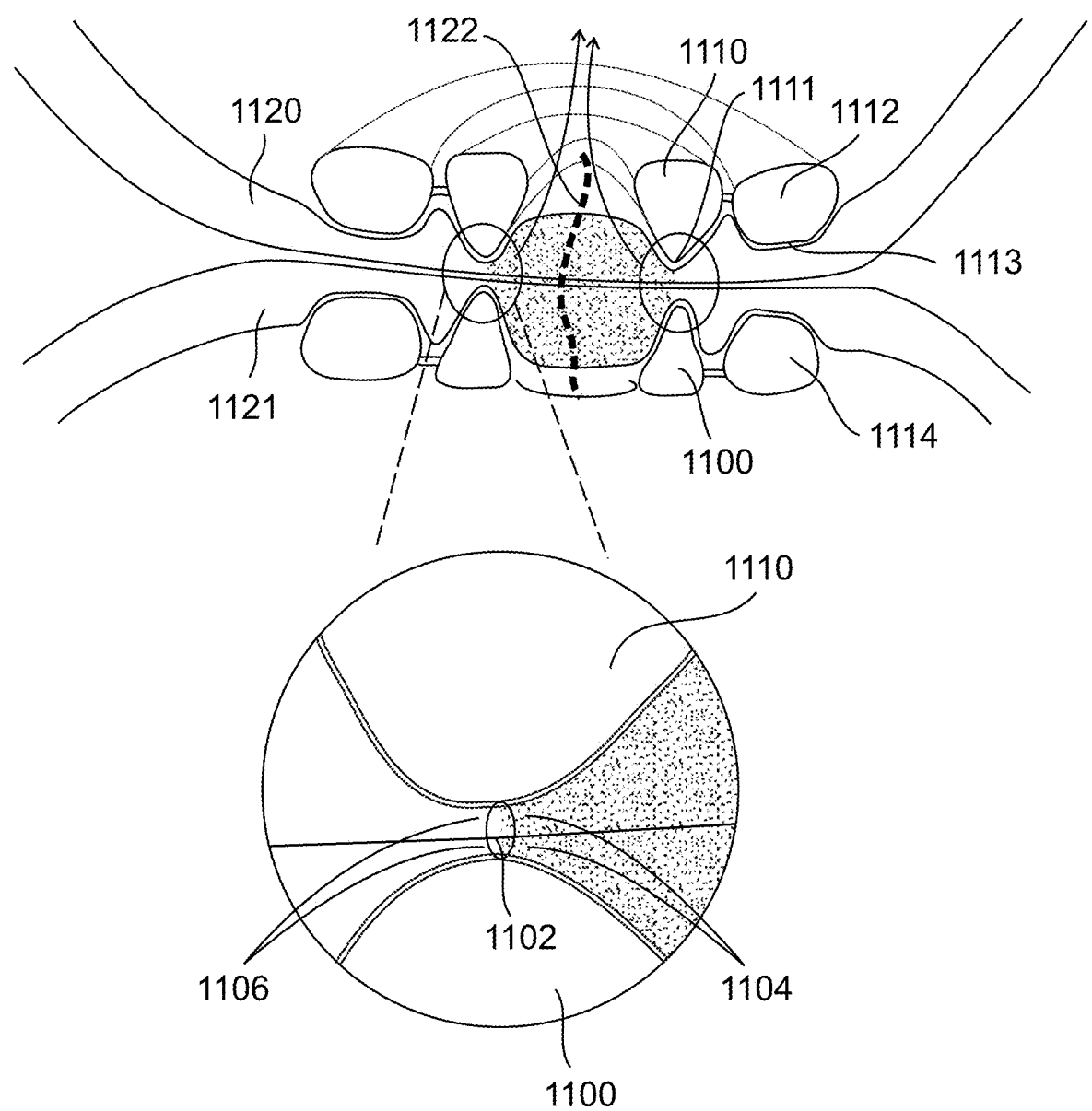
FIG. 11 illustrates anastomosis formation using a double ring device, according to some embodiments.

FIG. 11 illustrates anastomosis formation using a double ring device, according to some embodiments.

In some embodiments, inner rings 1100 and 1110 are configured to apply cut-through pressure, optionally gradually, onto the adjacent tissue walls 1120 and 1121, compressing tissue along anastomotic line 1102 (see enlarged view). Optionally, the pressure applied by inner rings 1100 and 1110 is high enough to affect blood perfusion along the anastomotic line. Optionally, the pressure applied by the inner rings gradually causes ischemia, until tissue region 1104 is damaged to an extent in which the applied pressure cuts through the tissue and a passage is formed between the adjacent walls.

Optionally, the pressure applied by the outer rings 1112 and 1114 is lower than a pressure that causes necrosis and/or other irreversible damage to the tissue. In some embodiments, blood perfusion to tissue 1106 outside the passage (e.g. externally to the anastomotic line, see enlarged view) is less affected by the inner cut-through pressure.

A potential advantage of less interrupted blood supply around the passage may potentially promote gradual healing of the tissue.

In some embodiments, outer rings 1112 and 1114 are positioned at each of walls 1120 and 1121 respectively to reduce leakage around the passage. Optionally, each of the outer rings presses against a tissue region circumferentially surrounding the passage.

Optionally, the applied pressure does not compromise blood perfusion.

Optionally, the pressure applied by outer rings 1112 and 1114 in the axial direction along which the passage is formed is low enough to keep the opposing outer rings 1112 and 1114 from direct interaction with other. A potential advantage of preventing the opposing outer rings from contacting each other may include maintaining the tissue viable, potentially providing for gradual adhesion of the tissue walls.

Optionally, the pressure applied by outer rings 1112 and 1114 is yet high enough to push down on the tissue walls with a force sufficient to block leakage, for example leakage caused at highly tensioned tissue regions and/or ischemic regions of the passage.

In some embodiments, the device comprises an element 1122 configured to draw the opposing inner rings and/or the opposing outer rings towards each other. In some embodiments, for example as illustrated herein, the element is a string, wire or cable interconnecting the opposing rings.

In some embodiments, element 1122 is rigid. Alternatively, element 1122 is non-rigid. In some embodiments, element 1122 is elastic.

In some embodiments, element 1122 is configured to exert an initial pulling force between the rings. Optionally, element 1122 is configured to be pulled on and/or shortened so as to approximate the opposing rings to each other. In some embodiments, a length of element 1122 defines a maximal distance between the opposing rings. In some embodiments, for example when element 1122 is a rigid, non-shapeable element, a length of element 1122 defines a minimal distance between the opposing rings.

In some embodiments, the outer ring is shaped to define a tissue contacting surface area 1113 (shown at a cross section) which is larger than a tissue contacting surface area 1111 of the inner ring. In some embodiments, the differently sized contact areas of the inner and outer rings set the level of pressure applied to the tissue, for example, for a similar magnitude of force, the inner ring will apply a higher pressure onto the tissue.

Figure 12:
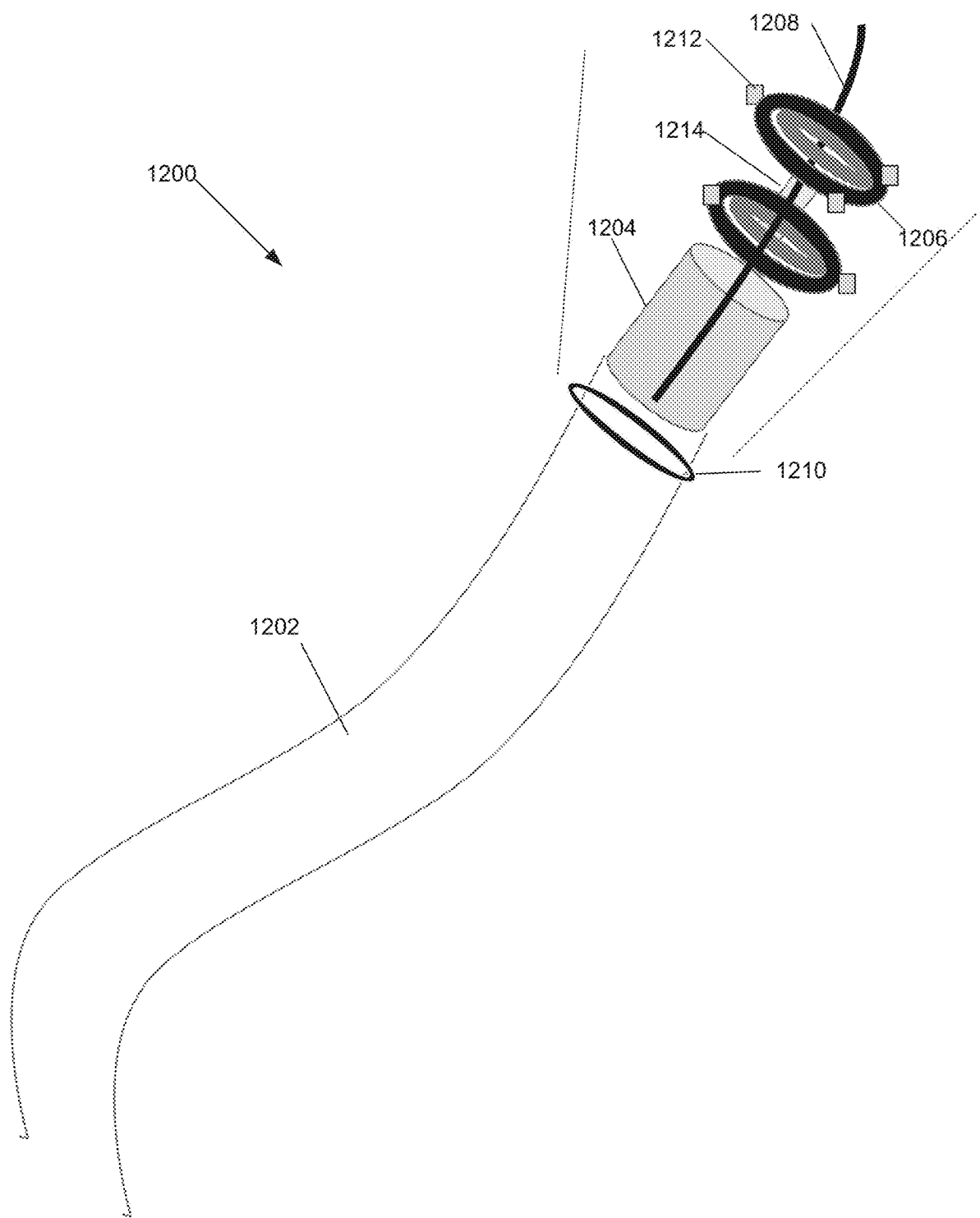
FIG. 12 schematically illustrates a kit for implanting an anastomosis device, according to some embodiments.

FIG. 12 schematically illustrates a kit for implanting an anastomosis device, according to some embodiments.

In some embodiments, kit 1200 comprises a shaft 1202, comprising a distal end portion 1204 on which anastomosis device 1206 is mounted. In some embodiments, shaft 1202 comprises or is configured to receive a guide wire 1208, over which device 1206 can be delivered to the anastomosis site.

In some embodiments, device 1206 comprises two sets of rings. Optionally, the ring sets are coupled by a central shaft 1214.

In some embodiments, shaft 1202 comprises an imager 1210, such as an ultrasound transducer.

In some embodiments, shaft 1202 is sized for insertion to and/or through body lumens, for example having a diameter between 0.5 cm and 3 cm, such as 1 cm, 2 cm, 2.5 cm, or intermediate, larger or smaller diameters. In some embodiments, shaft 1202 is flexible. Alternatively, shaft 1202 is rigid. Alternatively, shaft 1202 is rigid in some portions, and flexible in others.

In some embodiments, distal end portion 1204 is detachable from the shaft. Optionally, portion 1204 is disposable and can be replaced between uses, for example to be used with a new anastomosis device 1206 in the next implantation.

In some embodiments, kit 1200 comprises one or more sensors and/or leakage indicators 1212. Optionally, the leakage indicator is configured on device 1206 so as to be implanted with the device. Additionally or alternatively, leakage indicator 1212 is configured on shaft 1202. In some embodiments, leakage indicator 1212 comprises a temperature sensor, for assessing a local tissue temperature which may change in the presence of leakage. In some embodiments, leakage indicator 1212 comprises a chemical detector such as a PH meter for detecting changes in pH levels which may occur in the presence of leakage (such as in the presence of leaking bile, pancreatic content and/or stomach content).

In some embodiments, kit 1200 is configured for delivery of medication and/or sealant material (e.g. glue) to the anastomosis site, for example by shaft 1202 having one or more channels for conducting fluid. Optionally, shaft 1202 provides for irrigation.

In some embodiments, kit 1200 is configured to be coupled to an endoscope, for example by threading shaft 1202 over the endoscope. Optionally, shaft 1202 is cannulated along at least a portion of its length.

FIGS. 13A-D schematically illustrate a leakage-reducing ring for use with a stapler device, according to some embodiments.

Figure 13A:
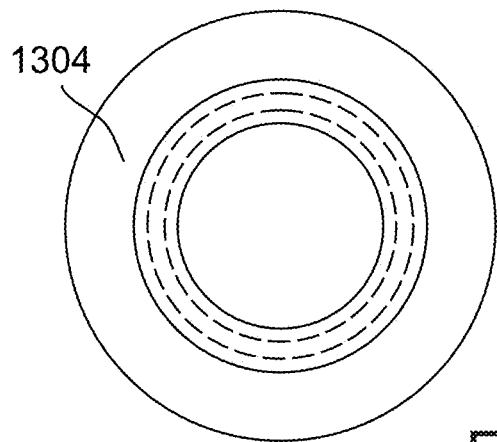
FIGS. 13A-D schematically illustrate a leakage reducing ring for use with a stapler device, according to some embodiments.
Figure 13B:
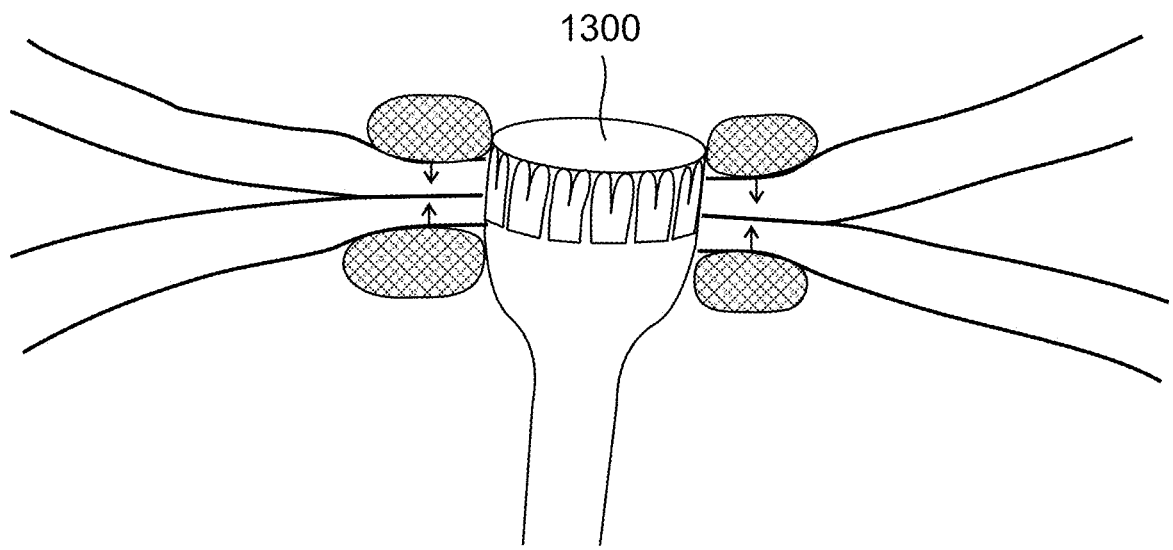
Figure 13C:
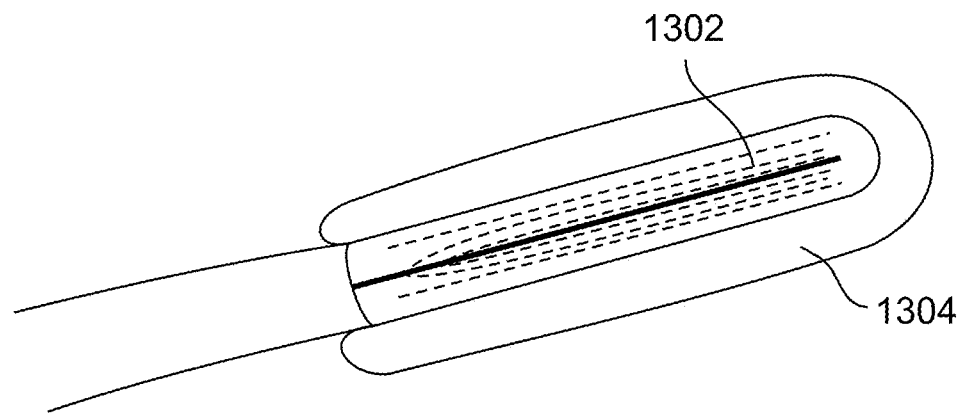
Figure 13D:
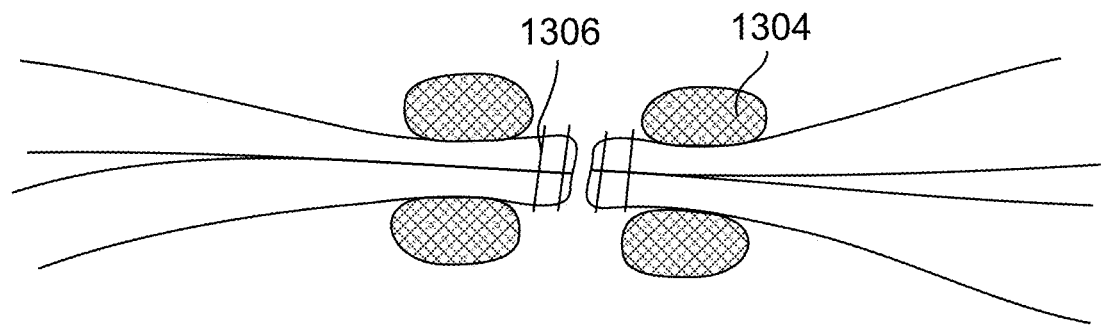

In some embodiments, a stapler device 1300 for example a circular stapler device 1300 as shown in FIG. 13B and/or a linear stapler device 1302 for example as shown in FIG.

13C is used with a leakage-reducing ring 1304. Optionally, stapler device 1300 and/or 1302 may include devices known in the art.

In some embodiments, leakage-reducing ring 1304 is shaped and/or sized to fit around the stapler device. In some embodiments, ring 1304 comprises an inflatable balloon ring, for example as described herein above.

In some embodiments, the stapler device is configured to deploy clips 1306 (see FIG. 13D) in the tissue, and ring 1304 is positioned externally (e.g. peripherally, see FIG. 13A) to the clips to reduce leakage around the passage formed by stapler device 1300 and/or 1302.

Figures 14A, 14B:
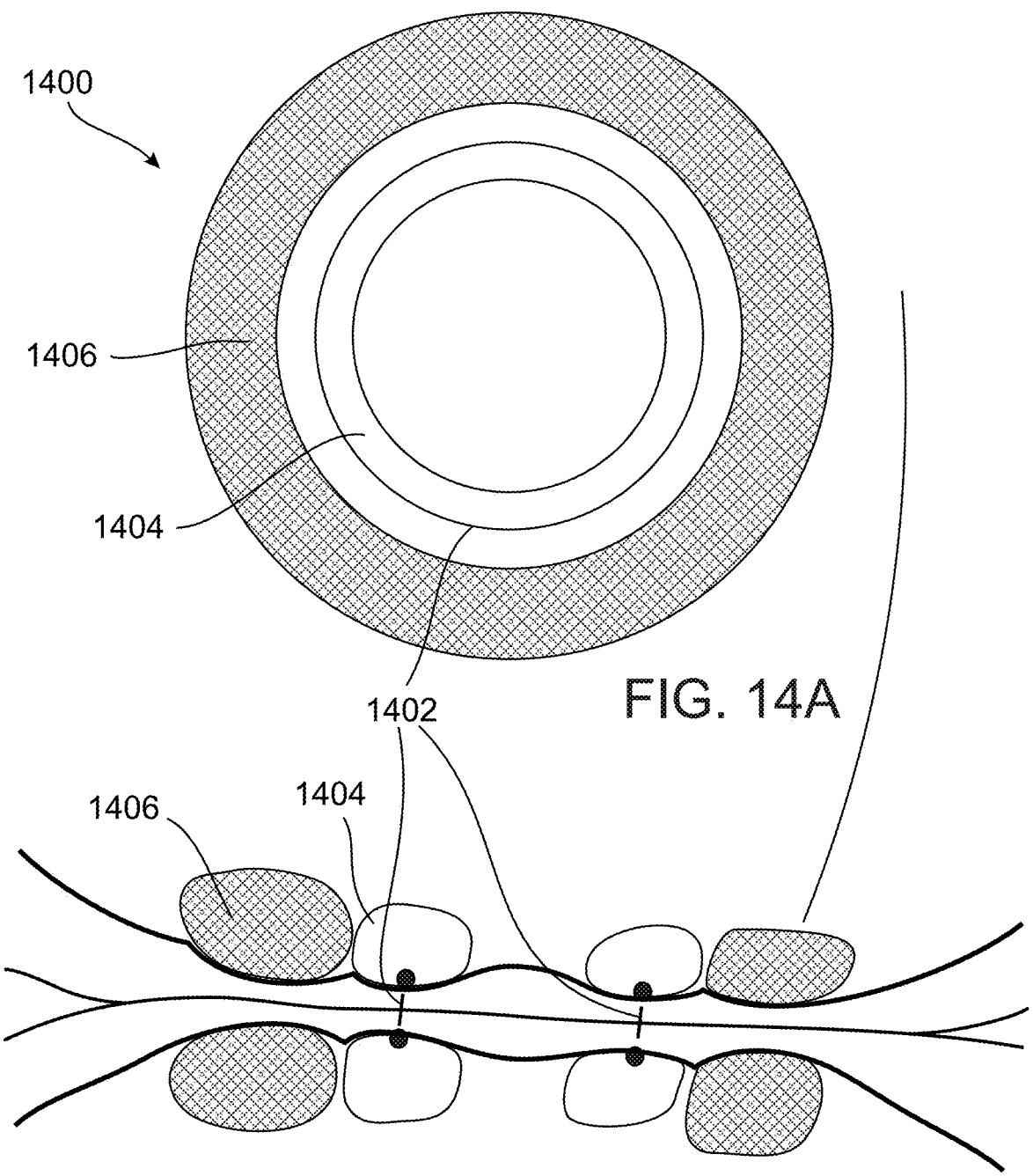
FIGS. 14A-B schematically illustrate an anastomosis device comprising a cutting blade, according to some embodiments.

In some embodiments, a cutting ring for example as described in FIGS. 14A-B may be used with and/or instead of an inner ring of the anastomosis device.

In some embodiments, a peripheral ring is placed about a stapled anastomosis. For example, when treating a rectal stump, after resection of segments of the large bowel, the ends may be stapled together (e.g. using a circular stapler), and a peripheral ring is placed outwardly relative to the staples to reduce leakage.

FIGS. 14A-B schematically illustrate an anastomosis device comprising a cutting blade, according to some embodiments.

In some embodiments, anastomosis 1400 device comprises a cutting blade 1402. In some embodiments, blade 1402 comprises a wire, such as a metal wire.

Optionally, the wire is electrically conductive. In some embodiments, the wire is configured to be heated so at to ablate tissue to cut through it. In some embodiments, the heated wire is configured to induce coagulation of tissue.

In some embodiments, blade 1402 is ring shaped. Alternatively, blade 1402 is elliptical, linear, or comprises any other shape suitable for producing a cut through the tissue.

In some embodiments, blade 1402 is embedded and/or otherwise attached to an inner ring 1404 of device 1400. Optionally, the anastomosis is produced by a one or both of: a pressure applied by inner ring 1404 onto the adjacent tissue walls, and/or a cutting force applied by blade 1402. Optionally, the passage-forming pressure and/or cutting force are applied immediately following implantation of the device and/or at a later stage, for example, 1 2, 3 4 days or intermediate, longer or shorter time period after implantation.

In some embodiments, blade 1402 is electrically conductive and inner ring 1404 comprises non-conductive material.

In some embodiments, cutting action by blade 1402 is initiated by conducting and/or inducing a current through the wire. Optionally, the current is induced and/or delivered endoscopically.

In some embodiments, the cutting action is initiated only after at least partial adhesion of the serosal surfaces of the adjacent tissue walls has been achieved by the leakage-reducing outer ring 1406.

FIGS. 15A-17B schematically illustrate deployment of a leakage-reducing device at a leaking site of a previously formed anastomosis, according to some embodiments.

Figure 15A:
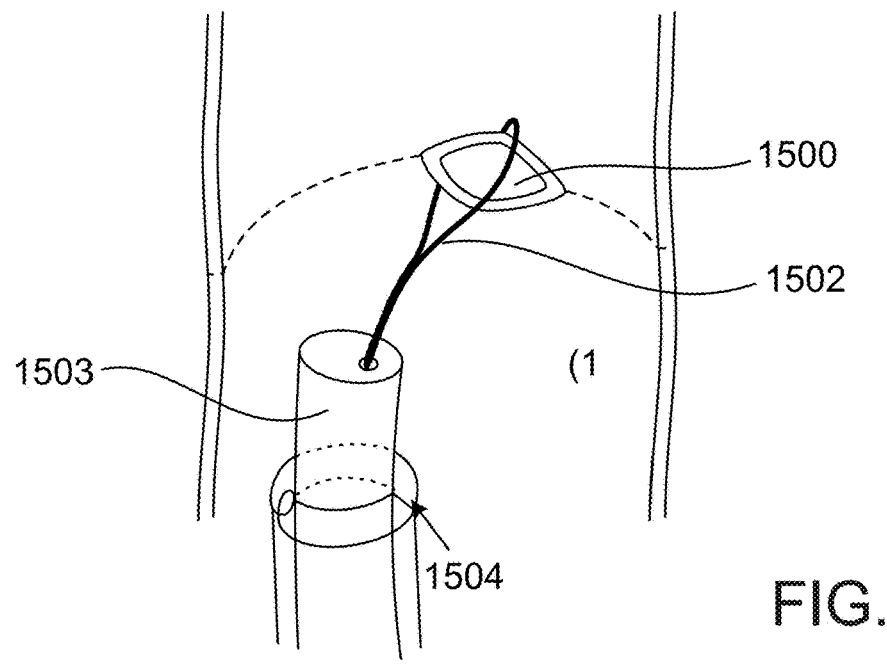
FIGS. 15A-C illustrate endoscopic deployment of a leakage reducing device at a leaking site, according to some embodiments.
Figure 15B:
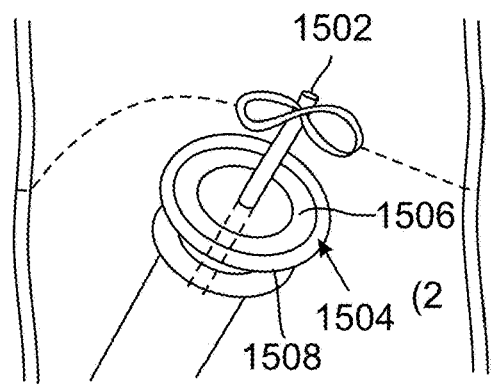
Figure 15C:
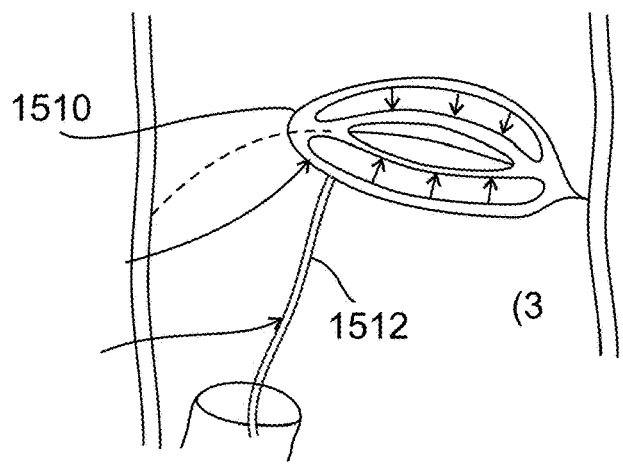

FIGS. 15A-C illustrate endoscopic deployment of a leakage reducing device at a leaking site 1500, according to some embodiments. In an example, the leaking site is approached from the bowel lumen.

In some embodiments, as shown for example in FIG. 15A, tissue adjacent the leaking site is grasped by advancement of an endoscopic grasper 1502 and/or other tool suitable for obtaining hold of the tissue during deployment of the leakage-reducing device. Optionally, the grasping tool is delivered through a working channel of an endoscope 1503.

In some embodiments, once the leaking site (i.e. edges thereof) was grasped by the endoscopic grasper, as shown for example in FIG. 15B, device 1504 is advanced over grasper 1502 and positioned across the adjacent tissue walls at the leaking site 1500, for example as shown in FIG. 15C. Optionally, device 1504 is delivered in an "over the scope" approach.

In some embodiments, device 1504 comprises a set of two opposing rings 1506 and 1508, optionally drawn together by a shape memory frame 1510. The rings may be inflatable, magnetically activated and/or shape-memory activated. FIG. 15C schematically illustrates inflation of the rings, for example via inflation tube 1512, for applying compression onto the tissue at the leaking site. In some embodiments, device 1504 remains implanted until the adjacent tissues adhere to each other enough to substantially reduce or prevent further leakage.

Figure 16A:
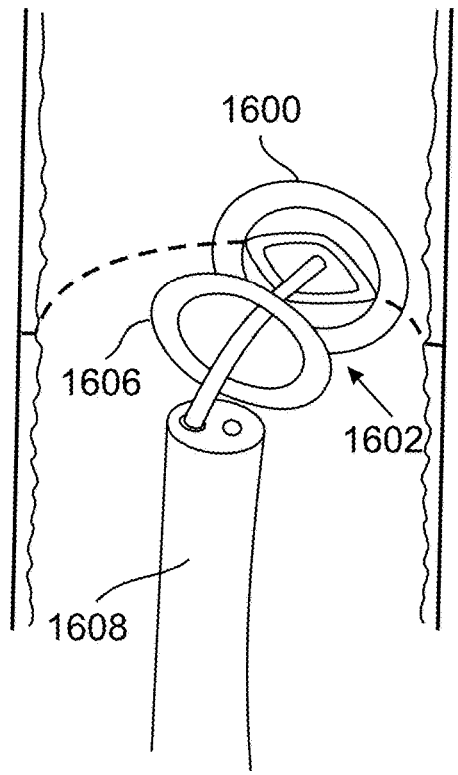
FIGS. 16A-C illustrate endoscopic deployment of a leakage reducing device at a leaking site by advancing at least a portion of the device across the leaking opening in the tissue, according to some embodiments.
Figure 16B:
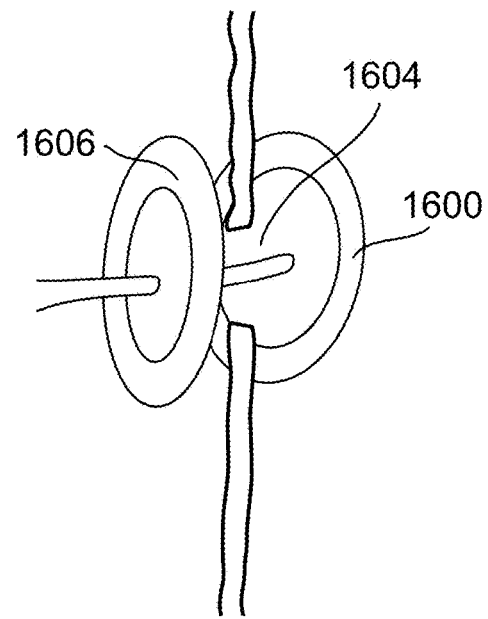
Figure 16C:
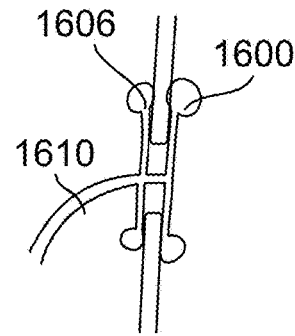

FIGS. 16A-C illustrate deployment of a leakage reducing device at a leaking site by advancing at least a portion of the device across the leaking opening in the tissue, according to some embodiments. FIG. 16A schematically illustrates an endoscopic view of the deployment, FIG. 16B schematically illustrates a side view of the device deployed across the adjacent tissue walls, and FIG. 16C schematically illustrates the deployed device at a cross section.

In some embodiments, a "leaking site" may refer to one or more openings in the GI tract such as a leaking anastomosis, a perforation at any segment of the GI tract, and/or an opened fistula.

In some embodiments, a first ring 1600 of device 1602 is advanced across leaking opening 1604 to be positioned at the first tissue wall (optionally at the extra-luminal side of the tissue wall), while the second opposing ring 1606 remains at the second tissue wall (of the lumen that was approached by the endoscope 1608, at the inner mucosal side of the wall). In some embodiments, the rings are inflated to apply compression onto the tissue and block the leaking site tightly enough to reduce or prevent the leakage. Optionally, the rings are inflated to a level sufficient to maintain the rings in place and reduce migration of the rings. In some embodiments, device 1602 is maintained at the leaking site for a time period of between 1-16 weeks, such as 2 weeks, 5 weeks, 9 weeks or intermediate, longer or shorter time periods to allow for healing and/or sealing of the leaking site.

In some embodiments, the rings are formed or are at least partially coated by a fluid tight material, such as nylon, Teflon, PTFE Goretex and/or other sealing material. In some embodiments, the device is formed of biodegradable materials.

In some embodiments, a tube 1610 is positioned to extend from the leaking site (e.g. from the center of the rings) to a natural orifice through which the delivery endoscope was inserted, for draining fluid away from the leaking site (e.g. from the extra-luminal space). Optionally, clearing of the fluid allows for lavage of the site. In some embodiments, tube 1610 provides for unidirectional drainage of the cavity containing fluid and/or pus and/or any other content that leaked from the GI tract to outside the body. Alternatively, the tube directs the fluid back into the lumen of the GI tract. Optionally, the tube is shaped to seal the hole at the leaking site. Optionally, the tube itself does not provide the sealing but is attachable to a separate sealing mechanism. In some embodiments, unidirectional drainage is enabled by one or more valves placed along the tube. In some embodiments, a tube such as 1610 may extend from an abscess external to the GI tract to outside the body, optionally via the GI tract, to provide for draining of fluid. The tube may extend along a full length of the GI tract or, alternatively, along a section of the GI tract.

In some embodiments, the tube is configured to drain extra-luminal fluid into the GI tract, optionally continuing via the GI tract to outside the body. In some embodiments, a tube extending to the extra-luminal space may provide for rinsing and/or irrigation of the extra-luminal space, which may contribute to healing of local infections. Optionally, in such case, the tube is operably attached to a rinsing module and/or vacuum or suction modules. In some embodiments, the tube comprises a plurality of separate inner channels (e.g. 2 or 3 channels) allowing for drainage, rinsing and/or vacuum. In some embodiments, at least one of the inner channel comprises a diameter large enough to allow passing of a flexible scope through, enabling, for example, inspection of the extra luminal cavity and/or other endoscopic operations.

In some embodiments, the leakage reducing rings of FIGS. 16A-C may be implanted simultaneously or following implantation of an anastomosis producing device for example as described hereinabove.

In some embodiments, if the leakage site is at an enteroatmospheric fistula, the device may be deployed from the atmospheric side and into the bowel to seal the opening, without the need for an endoscopic procedure and/or other internal approach.

Figures 17A, 17B:
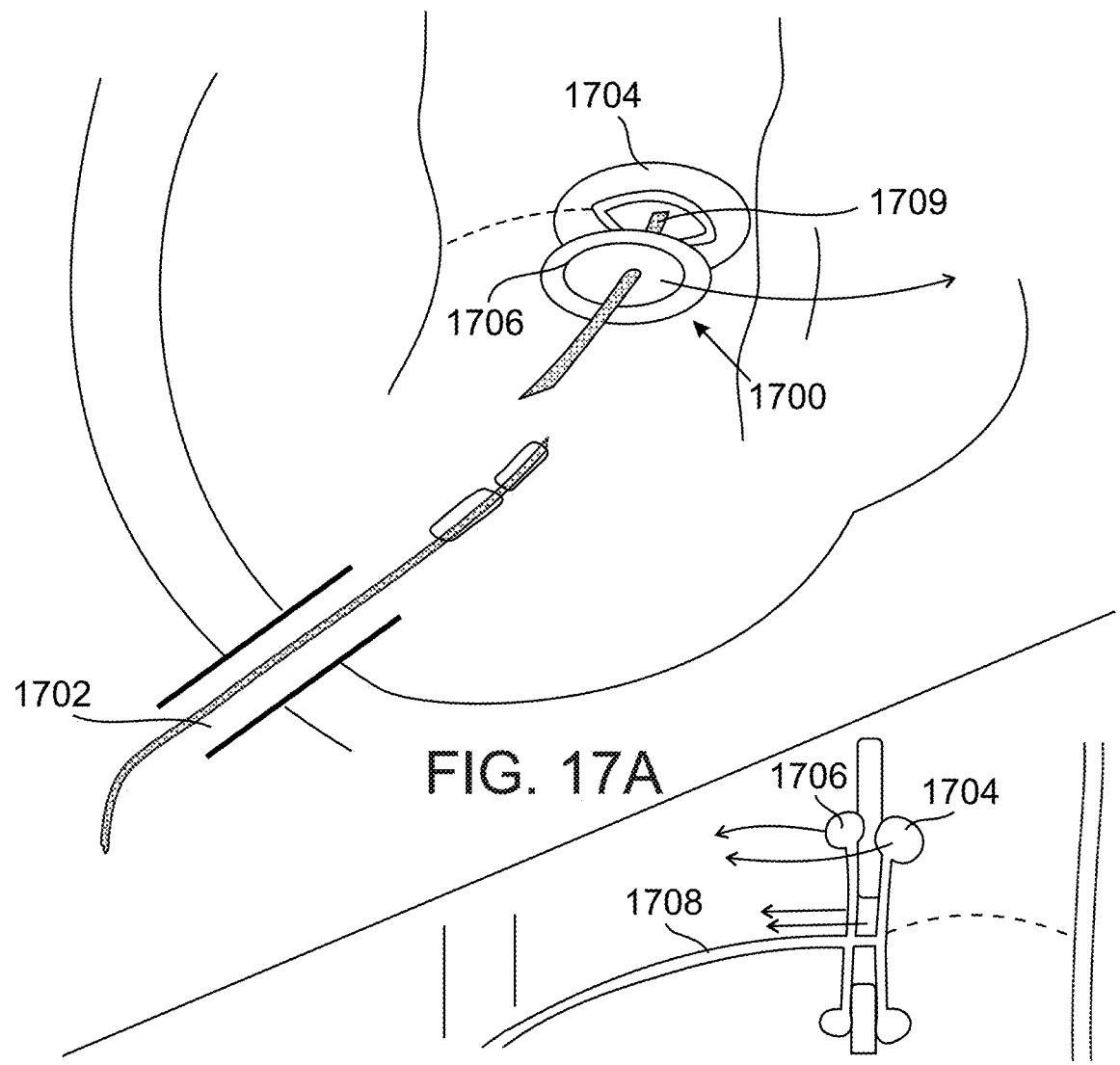
FIGS. 17A-B illustrate a non-endoscopic approach, e.g. a laparoscopic and/or thorascopic approach for deployment a leakage reducing device at a leaking site, according to some embodiments.

FIGS. 17A-B illustrate a non-endoscopic approach, e.g. a laparoscopic and/or thoracoscopic approach for deployment of a leakage reducing device at a leaking site, according to some embodiments.

In some embodiments, as shown for example in FIG. 17A, device 1700 is delivered percutaneously via a trocar 1702 to the leaking site. Optionally, opposing rings 1704 and 1706 are deployed via the anastomosed tissue walls to occlude the opening through which leakage was detected. Optionally, an optical scope (not shown herein) is disposed at a distal end of a shaft 1709 interconnecting between the opposing ring sets of the device, for detecting the leakage. Shaft 1709 may be flexible, rigid or semi-rigid. Optionally, the abdominal or thoracic cavities are inflated by CO2 prior to insertion of the device to and/or simultaneously during insertion (e.g. via a designated tube) to facilitate visualization.

FIG. 17B shows the deployed device at a cross section. In some embodiments, a draining tube 1708 is positioned to extend from the leaking site to outside of the body (e.g. via the trocar, through the skin of the abdominal or thoracic wall) to clear fluid away from the site.

Figure 18:
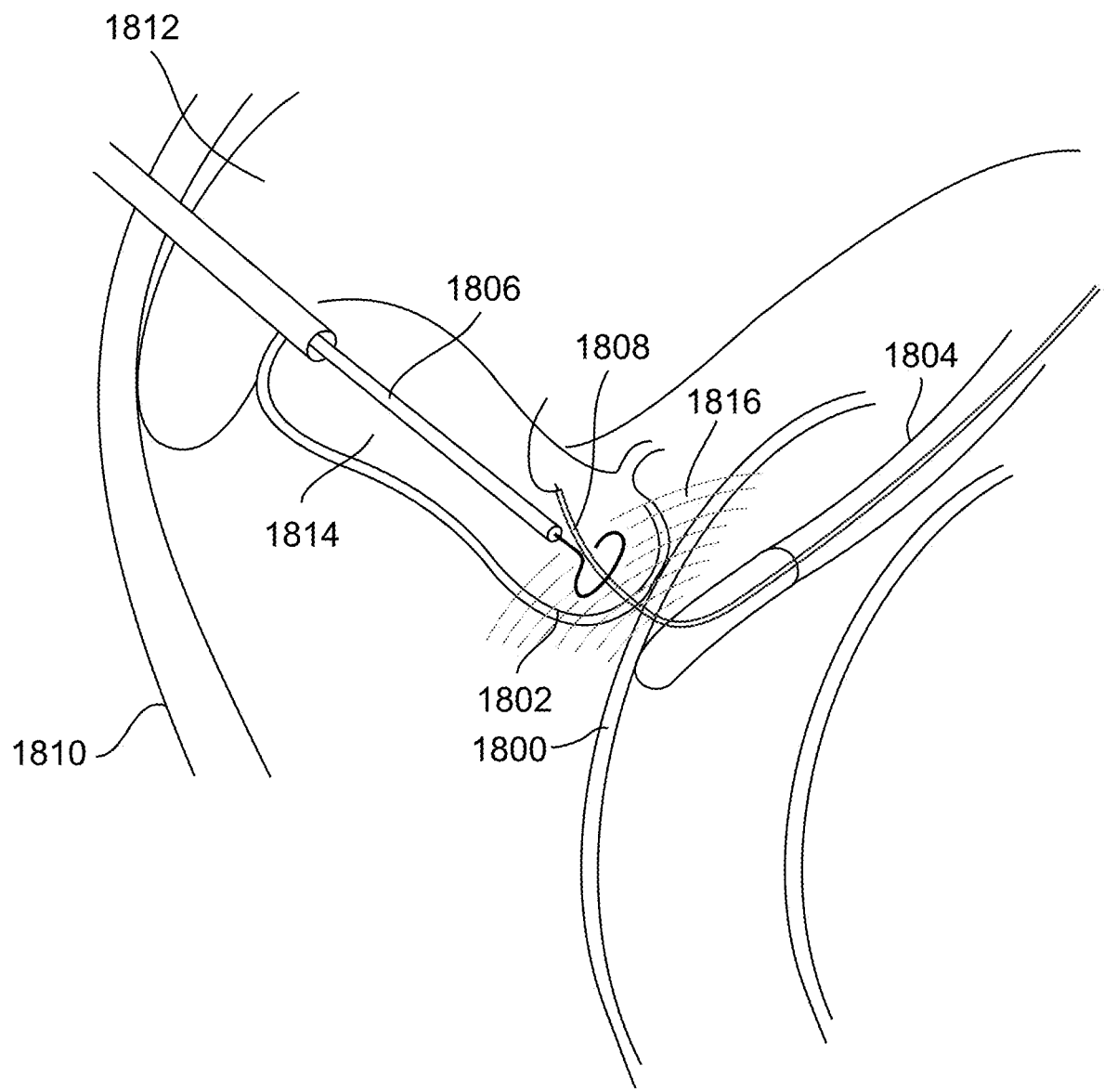
FIG. 18 illustrates a combined endoscopic and percutaneous implantation approach, in accordance with some embodiments.

FIG. 18 illustrates a combined endoscopic and percutaneous approach, in accordance with some embodiments. In the example shown herein, the duodenum wall 1800 is approached endoscopically, and the gallbladder wall 1802 is approached percutaneously, for example via the skin and abdominal wall 1810, through the liver 1812, and into the lumen of the gallbladder 1814.

In some embodiments, the opposing tissue walls are approximated towards each other, and an initial path is produced by penetrating the tissue from one side to another against counter pressure applied by the opposing side. In this example, the duodenum wall 1800 and the gallbladder wall 1802 are approximated towards each other, for example using tools introduced from both directions, such as an endoscopic working channel 1804 inserted into the duodenum lumen and/or a catheter 1806 (e.g. a transhepatic tube) introduced into the gallbladder lumen. In some embodiments, both walls are pushed towards each other. Alternatively, a first wall is pushed towards the second, while the second remains substantially in place.

In some embodiments, an initial path through the approximated tissue walls is produced by a needle 1808, for example introduced through an endoscopic working channel 1804 and/or through catheter 1806. Penetrating tissue against counter force may accelerate penetration and/or provide for a more accurate penetration location, e.g. a location suitable for later receiving the leakage reducing device.

In some embodiments, the initial path is dilated, for example dilated enough to provide for introducing of at least a portion of the leakage reducing device through (e.g. dilated enough for introducing a set of rings for positioning over at one tissue wall through).

In some embodiments, approximating and/or penetrating of the tissue walls is performed under image guidance, for example using endoscopic ultrasound (EUS) 1816 and/or fluoroscopy.

In some embodiments, the walls are approximated until contact between the two walls is established at least in an area surrounding the site of penetration.

Figure 19:
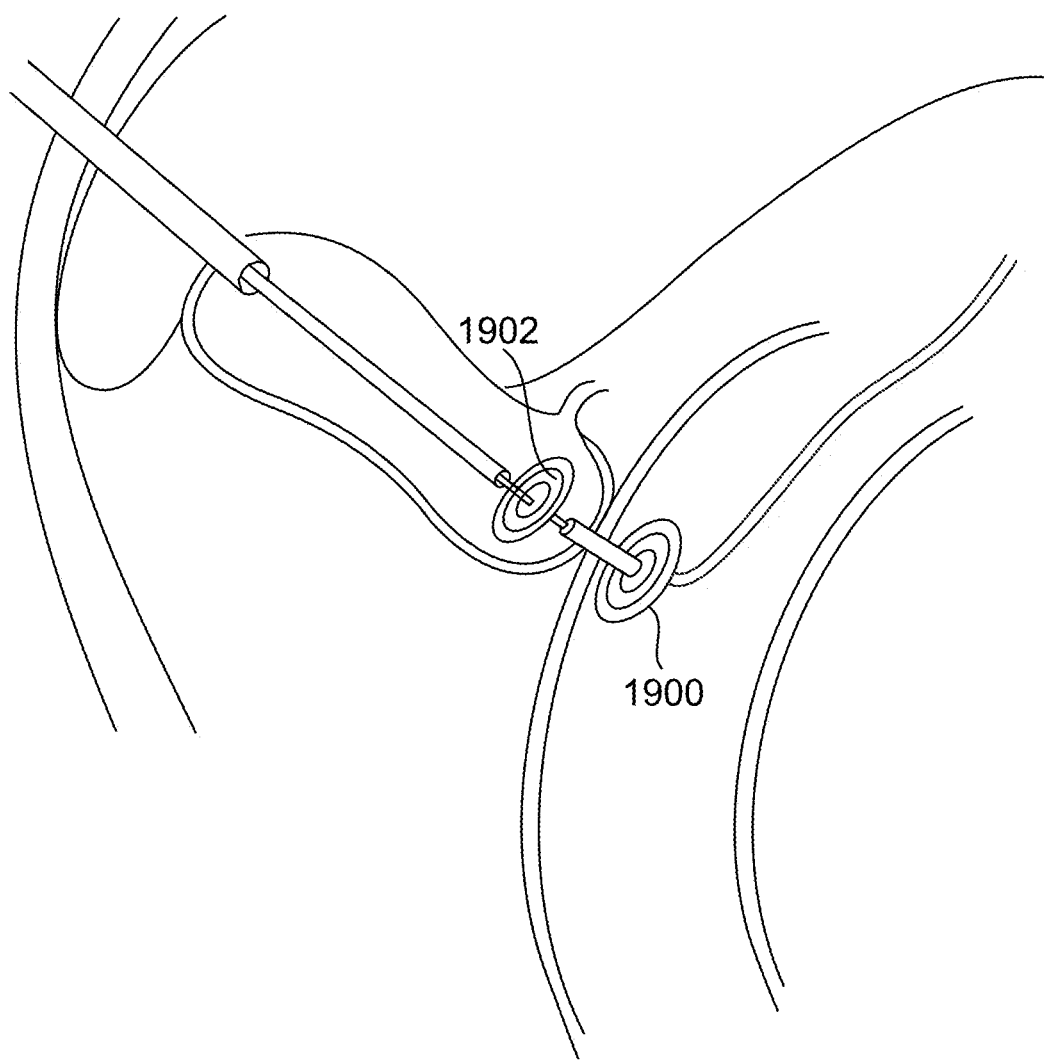
FIG. 19 illustrates implanting of a leakage reducing device in which portions of the device are separately introduced to the opposing tissue walls, in accordance with some embodiments.

FIG. 19 illustrates implanting of a leakage reducing device in which portions of the device are separately introduced to the opposing tissue walls, in accordance with some embodiments.

In some embodiments, using a delivery system and/or method for example as described in FIG. 18, device portions such as a first set of rings 1900 and a second set of rings 1902 are each introduced to their respective tissue wall independently of each other. For example, the first set of rings 1900 is introduced to the duodenum wall, optionally endoscopically, and the second set of ring 1902 is introduced to the gallbladder wall, optionally percutaneously.

In some embodiments, the separate device portions are introduced simultaneously. Alternatively, the separate device portions are introduced one after the other.

In some embodiments, when the separate device portions are positioned near and/or at the leakage site, a coupling between the device portions is produced, for example by utilizing magnetic attraction between the separate device portions. In some embodiments, the coupling is configured to align and/or hold and/or approximate the opposing ring sets to each other.

Optionally, the coupling comprises a cable or wire extending between the device portions. Additionally or alternatively, an indirect coupling for example using magnetic force as described hereinabove is used.

In some embodiments, coupling is performed under image guidance, for example using endoscopic ultrasound and/or fluoroscopy and/or visual video guidance, such as using a camera mounted on an endoscope.

Figure 20:
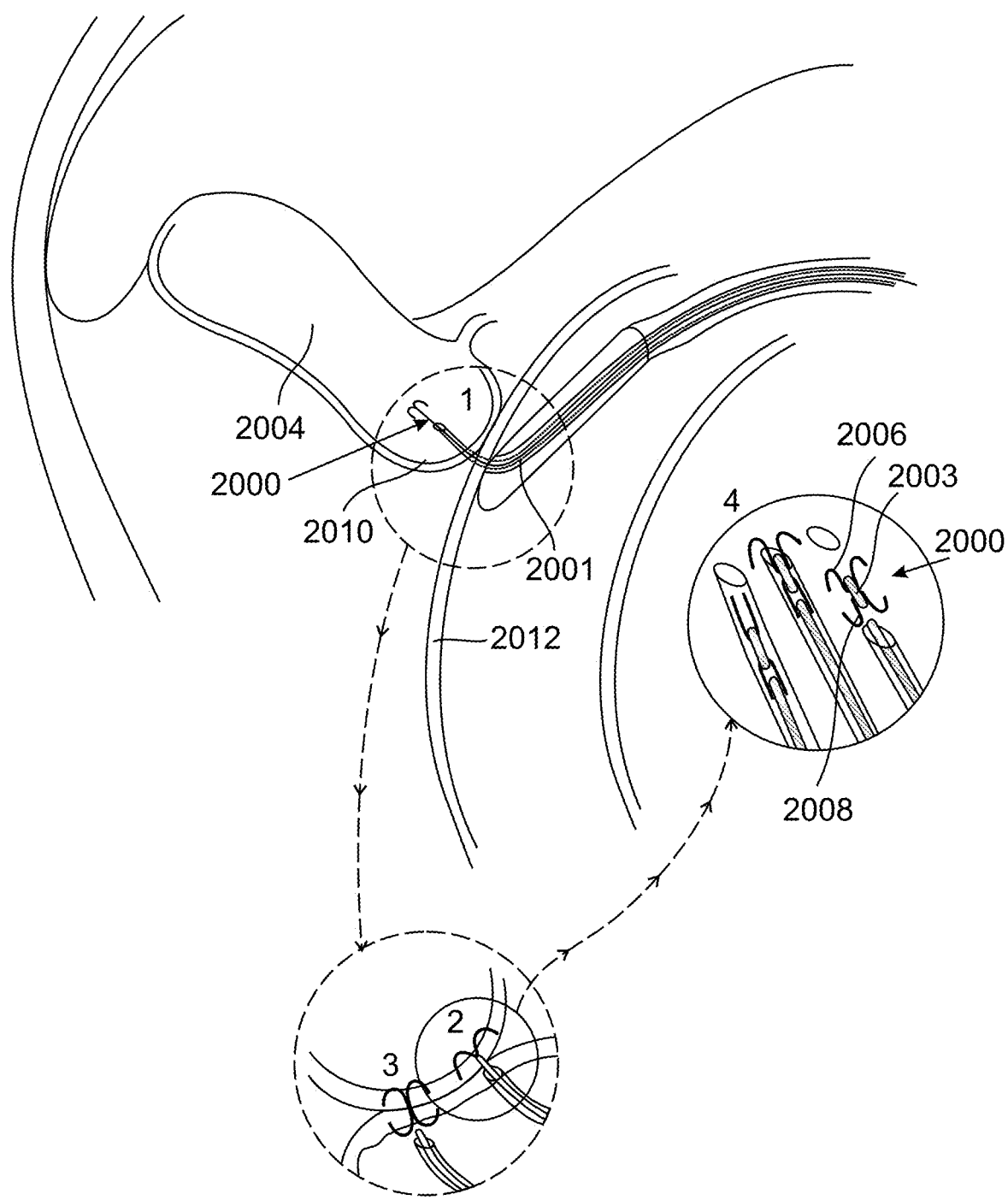
FIG. 20 illustrates approximating of the opposing tissue walls using a tissue adjoining device, according to some embodiments.

FIG. 20 illustrates approximating of the opposing tissue walls using a tissue adjoining device, according to some embodiments.

In some embodiments, optionally prior to introducing of the leakage reducing device, one or more tissue adjoining devices such as clips 2000 are deployed adjacent the leakage site to approximate and/or further to hold the opposing tissue walls to each other. In some embodiments, clip 2000 comprises two sets of hooks—a first set of hooks 2006 and a second set of oppositely facing hooks 2008. In some embodiments, clip 2000 comprises a main body 2003, and hooks 2006 and 2008 are coupled to the distal and proximal ends of the main body, respectively.

In some embodiments, in addition or instead of the second set of hooks 2008, any elastic element that is configured to spring outwardly from a collapsed configuration to a perpendicular position relative to the long axis of needle 2001 may be used.

In an exemplary insertion method, clip 2000 is introduced through hollow needle 2001 to the gallbladder lumen 2004. In some embodiments, first set of hooks 2006 is released to be deployed at the gallbladder wall 2010. Optionally, retraction of needle 2001 actuates releasing of the hooks from needle 2001 (for example as shown in view "1"). In some embodiments, needle 2001 is further retracted, pulling hooks 2006 against the tissue of the gallbladder wall, for example until the hooks at least partially penetrate the mucosa (for example as shown in view "2"). Optionally, at this stage, further retraction of needle 2001 beyond the duodenum wall 2012 actuates releasing of the second of set of hooks 2008 for deployment at the duodenum wall (for example as shown in view "3"). Optionally, when needle 2001 is retracted further, clip 2000 detaches and remains deployed at the site, coupling the two adjacent walls to each other.

In some embodiments, for example as shown in view "4", the hooks of clip 2000 are resilient such that they spring outwardly from a compressed state within needle 2001 into a deployable configuration upon withdrawing of the needle.

In some embodiments, hooks 2006 and/or 2008 comprise memory shape material, such as nitinol.

In some embodiments, clip 2000 comprises bioabsorbable materials. Optionally, clip 2000 maintains hold of the tissue walls to each other until it is dissolved, for example until after deployment of the leakage reducing device.

Tissue adjoining devices for example as described hereinabove may be used in any other procedure in which tissue walls are to be approximated towards each other, for example for approximating segments of the GI tract to each other, approximating an organ to a segment of the GI tract, approximating the abdominal wall to a segment of the GI tract and/or other applications in which tissue walls or portions thereof are approximated to each other.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention.

Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

What is claimed is:

1. An anastomosis device configured to reduce leakage, comprising:
   a first set of rings sized to be positioned at a first tissue wall;
   a second set of rings sized to be positioned at a second tissue wall, the second tissue wall being adjacent the first tissue wall; and
   drawing means for approximating the ring sets towards each other;
   wherein each set of rings comprises:
      an inner ring having a tissue-facing surface;
      an outer ring having a tissue-facing surface; and
      a coupling between the inner ring and the outer ring for aligning the inner and outer rings with respect to each other; the inner ring and the outer ring being co-axial, the outer ring circumferentially surrounding the inner ring;
   wherein when the device is deployed in tissue and the rings sets are approximated towards each other by the drawing means:
   tissue-facing surfaces of the inner rings overlap to compress tissue in-between, and tissue-facing surfaces of the outer rings overlap;
   the inner rings apply a first pressure between them onto the first and second tissue walls, the first pressure sufficient to gradually form a passage between the first and second tissue walls; and the outer rings apply a second pressure between them onto the first and second tissue walls, the second pressure applied radially outwardly relative to the first pressure, the second pressure sufficient to reduce leakage in a vicinity of the passage.

2. The device according to claim 1, wherein one or both of the inner ring and the outer ring of each set is inflatable.

3. The device according to claim 2, wherein pressure applied by the inner ring and the outer rings onto the tissue is controlled by inflation pressures.

4. The device according to claim 1, wherein the drawing means comprise an inner construction incorporated in each of the ring sets.

5. The device according to claim 4, wherein the inner construction comprises magnetic material incorporated in or mounted on one or both of the inner ring and the outer rings of each set, the magnetic material positioned to induce magnetic attraction between the inner rings of the two sets and/or between the outer rings of the two sets.

6. The device according to claim 4, wherein the inner construction comprises shape memory material incorporated in one or both of the inner ring and the outer rings of each set, the shape memory material shaped and positioned so that deformation of the shape memory material changes a level of pressure applied by one or both of the inner ring and the outer rings onto the tissue.

7. The device according to claim 1, wherein the drawing means comprise an elongated element which extends between the two sets of rings, interconnecting the two sets.

8. The device according to claim 7, wherein the elongated element is one of: a string, wire or cable.

9. The device according to claim 7, wherein the elongated element is tensioned to set at least an initial pulling force between the—inner rings of the two sets and/or between the outer rings of the two sets.

10. The device according to claim 1, wherein the coupling between the inner ring and the outer ring comprises one or more bridging elements extending between the inner ring and the outer ring.

11. The device according to claim 1, wherein the coupling between the inner ring and the outer ring comprises an adhesive attaching the at least a portion of an outer lining of the inner ring to at least a portion of an inner lining of the outer ring.

12. The device according to claim 1, wherein the device comprises a leakage indicator comprising a temperature sensor or a PH meter.

13. The device according to claim 1, wherein the device comprises one or more pressure sensors positioned at an interface between the tissue and one or both of the inner ring and the outer ring of each set, the pressure sensors configured to detect an actual pressure applied by the inner ring and/or the outer ring onto the tissue.

14. The device according to claim 1, wherein the device comprises one or more sensors configured for detecting a level of oxygen saturation of the compressed tissue.

15. The device according to claim 1, wherein the inner ring of each set further comprises a cutting wire.

16. The device according to claim 1, wherein one or both of the inner ring and the outer ring of each set comprises a toroidal shaped balloon.

17. The device according to claim 1, wherein a contact surface area of the outer ring with the tissue is larger than a contact surface area of the inner ring with the tissue.

18. The device according to claim 1, wherein the drawing means comprise an interconnecting element configured to be tensioned and/or shortened to approximate the ring sets towards each other.

19. The device according to claim 1, wherein the first pressure is sufficient to cut through tissue to gradually form the passage, and the second pressure is high enough to reduce leakage in a vicinity of the passage yet low enough to avoid ischemia and tissue necrosis.

20. The device according to claim 1, wherein the tissue facing-surface of the inner ring of each set comprises a protrusion for applying increased pressure at a localized point.

21. The device according to claim 1, wherein the drawing means are configured to exert a pulling force sufficient to produce the first pressure and the second pressure.

22. An anastomosis device configured to reduce leakage, comprising:
a set of two rings for positioning over adjacent first and second tissue walls, each ring comprising at least:
a first chamber configured to apply a first pressure onto a respective tissue wall out of the first and second tissue walls, the pressure sufficient to form a passage between the first and second tissue walls; and
a second chamber configured to apply a second pressure onto the respective tissue wall out of the first and second tissue walls, the pressure applied radially outwardly relative to the first pressure, the second pressure sufficient to reduce leakage in a vicinity of the passage.

23. The device according to claim 22, wherein the chambers are inflatable.

24. The device according to claim 22, wherein each ring out of the set of two rings further comprises a third chamber configured to apply a third pressure onto the respective tissue wall, the third pressure lower than the second pressure.

25. An anastomosis device configured to reduce leakage, comprising:
a first set of structures shaped and sized to be positioned at a first tissue wall;
a second set of structures shaped and sized to be positioned at a second tissue wall, the second tissue wall being adjacent the first tissue wall; and
an element configured to draw the sets towards each other;
wherein each set of structures comprises an inner substantially closed shape, an outer substantially closed shape surrounding the inner shape, and a coupling element between the inner substantially closed shape and the outer substantially closed shapes, the coupling element configured to control a ratio between a first pressure applied by the inner substantially closed shape onto the tissue, and a second pressure applied by the outer substantially closed shape onto the tissue.

* * * * *